(12) United States Patent
Takayama

(10) Patent No.: US 11,351,298 B2
(45) Date of Patent: Jun. 7, 2022

(54) IRRIGATION FUNCTION-EQUIPPED SUCTION DEVICE

(71) Applicant: TAKAYAMA INSTRUMENT INC., Tokyo (JP)

(72) Inventor: Ryushi Takayama, Tokyo (JP)

(73) Assignee: TAKAYAMA INSTRUMENT INC., Tokyo (JP)

( * ) Notice: Subject to any disclaimer, the term of this patent is extended or adjusted under 35 U.S.C. 154(b) by 212 days.

(21) Appl. No.: 16/627,554

(22) PCT Filed: Jul. 10, 2018

(86) PCT No.: PCT/JP2018/026102
§ 371 (c)(1),
(2) Date: Dec. 30, 2019

(87) PCT Pub. No.: WO2019/013229
PCT Pub. Date: Jan. 17, 2019

(65) Prior Publication Data
US 2020/0215258 A1 Jul. 9, 2020

(30) Foreign Application Priority Data
Jul. 12, 2017 (JP) .............................. JP2017-136670

(51) Int. Cl.
*A61M 3/02* (2006.01)
*A61M 39/24* (2006.01)

(52) U.S. Cl.
CPC .......... *A61M 3/0283* (2013.01); *A61M 3/022* (2014.02); *A61M 39/24* (2013.01); *A61M 2210/0693* (2013.01)

(58) Field of Classification Search
CPC ........ A61M 1/0062; A61M 1/00; A61M 1/76; A61M 3/0283; A61M 2210/0693;
(Continued)

(56) References Cited

U.S. PATENT DOCUMENTS

| 6,932,788 B2 | 8/2005 | Kamiyama et al. |
| 9,259,519 B2 | 2/2016 | Fedenia et al. |

(Continued)

FOREIGN PATENT DOCUMENTS

| JP | 02-86560 U | 7/1990 |
| JP | 2001-245967 A | 9/2001 |
| JP | 4330753 B2 | 9/2009 |

OTHER PUBLICATIONS

International Search Report for PCT/JP2018/026102 dated Oct. 16, 2018 (PCT/ISA/210).

*Primary Examiner* — Emily L Schmidt
*Assistant Examiner* — Joshua Parker Reddington
(74) *Attorney, Agent, or Firm* — Sughrue Mion, PLLC

(57) ABSTRACT

An irrigation function-equipped suction device including a suction device body, a suction path, an irrigation path and a flexible tube. With communication or closing of the suction path and the flexible tube by a first switch mechanism, the irrigation path and the flexible tube are caused to be closed off from each other or to communicate with each other by a second switch mechanism. The first switch mechanism is provided in a first section inside the suction device body, and the second switch mechanism is provided inside the irrigation path between the conversion mechanism and the flexible tube. The closing valve included in the second switch mechanism is disposed at a position on a side opposite to the flexible tube relative to the first switch mechanism and the conversion mechanism.

9 Claims, 21 Drawing Sheets

(58) Field of Classification Search
CPC ........ A61M 1/774; A61M 1/77; A61M 3/022; A61M 39/24; A61M 1/772
See application file for complete search history.

(56) References Cited

U.S. PATENT DOCUMENTS

2001/0037082 A1* 11/2001 Kamiyama ......... A61M 1/0062
604/164.07
2011/0230823 A1 9/2011 Simonsen

* cited by examiner

IRRIGATION FUNCTION-EQUIPPED SUCTION DEVICE

CROSS REFERENCE TO RELATED APPLICATIONS

This application is a National Stage of International Application No. PCT/JP2018/026102 filed Jul. 10, 2018, claiming priority based on Japanese Patent Application No. 2017-136670 filed Jul. 12, 2017.

TECHNICAL FIELD

The present invention relates to an irrigation function-equipped suction device and specifically relates to an irrigation function-equipped suction device for use in the medical field such as brain surgery.

BACKGROUND ART

In brain or traumatic injury surgery, etc., the work for removing blood, body fluid, spinal fluid, bone fragments, etc., which are accumulated in a surgical site, such as the brain or a trauma injury, of a human body or an animal and the work for irrigating the surgical site to clean the surgical site may be needed.

As a medical instrument for use in the aforementioned surgery, etc., an irrigation function-equipped suction device is used.

A body of the irrigation function-equipped suction device has both a function that removes blood, etc., which are accumulated in a surgical site, such as the brain or a trauma injury, of a human body or an animal and a function that irrigates the surgical site to clean the surgical site.

Use of the irrigation function-equipped suction device enables a surgeon to repeat cleaning of a surgical site and suction from the surgical site with a surgical instrument such as a surgical knife or forceps in one hand and the irrigation function-equipped suction device in the other hand.

In particular, in delicate surgery, determination of when to perform suction from a surgical site and when to clean the surgical site is difficult for an assistant other than a surgeon.

The irrigation function-equipped suction device enables a surgeon to maneuver the irrigation function-equipped suction device with one hand at his/her judgement. Even where there is no suction/cleaning operation by an assistant, a surgeon can smoothly perform surgery on a surgical site using the irrigation function-equipped suction device.

Under the above circumstances, a variety of such irrigation function-equipped suction devices have been proposed.

A first conventional technique is an irrigation function-equipped suction device in which a plurality of valves called trumpet valves are provided perpendicularly to a longitudinal direction of irrigation and suction paths (Patent Literature 1). Switching between the irrigation function and a suction function can be made by pressing the trumpet valves with fingers.

In the case of the irrigation function-equipped suction device including trumpet valves, a surgeon needs to press the trumpet valves vertically with two or more fingers when making switching between the irrigation operation and the suction operation.

However, when the trumpet valves are pressed vertically with fingers, respective distal ends of the irrigation and suction paths easily move vertically. Therefore, the irrigation function-equipped suction device including trumpet valves has the problem of difficulty in performing precise surgery.

A second conventional technique is an irrigation function-equipped suction device having a structure in which an irrigation path is provided outside a suction tube body so as to merge into a side hole of the suction tube body, enabling irrigation and suction from a distal end of the suction tube body (Patent Literature 2).

The irrigation function-equipped suction device includes a valve for squashing an irrigation tube connected to the irrigation path. Also, the irrigation tube is supplied with water from an irrigation tube, and pressing the valve with a finger results in the irrigation tube being squashed and thus enables stopping irrigation, and opening the valve enables resuming irrigation.

Also, the suction tube body of the irrigation function-equipped suction device includes an opening portion that leads to atmosphere. Suction performed by the irrigation function-equipped suction device can be adjusted by closing the opening portion with a finger or moving the finger away from the opening portion.

However, there has been a problem in that when a sterilized irrigation tube is squashed, the squashed parts easily tightly stick together and the sterilized irrigation tube does not easily return to an original shape from the squashed shape. Also, the irrigation tube may be ruptured by repeatedly squashing the irrigation tube, which may cause a need to repair or replace the irrigation function-equipped suction device during surgery.

A third conventional technique that addresses the first and second conventional techniques has been proposed (Patent Literatures 3 and 4).

FIGS. 20 and 21 are schematic sectional views illustrating an irrigation function-equipped suction device 200 according to the third conventional technique.

The irrigation function-equipped suction device 200 disclosed in the third conventional technique includes a suction device body 202. A suction path 210 and an irrigation path 212 are provided inside the suction device body 202.

Also, a flexible tube 220 is provided in the suction device body 202. Suction or irrigation can be performed via a distal end 222 of the flexible tube 220, enabling removal of blood, etc., from a surgical site of a patient or cleaning the surgical site of the patient.

A rotation valve 230 that enables switching between connection of the suction path 210 to the flexible tube 220 and connection of the irrigation path 212 to the flexible tube 220 is provided in the suction device body 202.

A rotation lever 240 is provided at an upper portion of the suction device body 202. The rotation lever 240 includes a mechanism of interlocking with the rotation valve 230, and upon the rotation lever 240 being pressed with a finger, the rotation valve 230 rotates counterclockwise (see FIG. 21). On the other hand, upon the pressing of the rotation lever 240 with a finger being stopped, the rotation valve 230 rotates clockwise and thus returns to an original state (see FIG. 20).

As is clear from FIGS. 20 and 21, each of an irrigation function and a suction function of the irrigation function-equipped suction device 200 is implemented via a zero point that prevents irrigation and suction from being performed simultaneously.

Also, a flexible tube 232 is connected to the rotation lever 240 and a recessed suction pressure fine adjustment hole 234 is provided in the rotation lever 240. The suction path 210 is open to atmosphere through the suction pressure fine adjustment hole 234.

A suction force can also be adjusted by closing the suction pressure fine adjustment hole 234 with a finger or moving the finger away from the suction pressure fine adjustment hole 234.

In the case of each of the first and second conventional techniques, when the irrigation function-equipped suction device is used, it is necessary to control two or more valves simultaneously.

On the other hand, in the case of the third conventional technique, suction and irrigation can be switched to each other by maneuvering the single rotation lever 240, which is convenient.

Also, the flexible tube 220 and a suction tube (not illustrated) connected to the suction path 210 are linearly joined to each other.

Therefore, solid substances such as bone fragments sucked from the flexible tube are promptly discharged to the outside of the suction device body 202 through the inside of the suction tube. With the structure of the third conventional technique, solid substances are less accumulated inside the suction device body 202, enabling prevention of clogging of the inside of the suction tube by bone fragments, etc. sucked from the flexible tube 220.

Although not specifically illustrated, in the third conventional technique, in addition to the technique that switches between irrigation and suction via the single rotation valve 230, a technique that switches between irrigation and suction via a combination of the rotation valve 230 and a piston valve is disclosed.

Furthermore, in the third conventional technique, a technique in which a conduction path is provided in a direction orthogonal to respective longitudinal directions of the suction path 210 and the irrigation path 212 and the conduction path is moved vertically by a piston valve is also disclosed.

Upon the suction path 210 and the irrigation path 212 being brought into communication with each other by vertical movement of the piston valve, irrigation can be performed.

On the other hand, upon the conduction path being moved away from a conduction position and the suction path 210 and the irrigation path 212 being thus closed off from each other by vertical movement of the piston valve, irrigation is stopped.

A mechanism that adjusts a suction force on the suction path 210 side via the rotation valve 240 according to the operation of the piston valve is also disclosed in the third conventional technique.

CITATION LIST

Patent Literature

Patent Literature 1: U.S. Pat. No. 9,259,519
Patent Literature 2: Japanese Utility Model Publication No. 2-86560
Patent Literature 3: Japanese Patent Laid-Open No. 2001-245967
Patent Literature 4: Japanese Patent No. 4330753

SUMMARY OF INVENTION

Technical Problem

As a result of study of an irrigation function-equipped suction device typified by the third conventional technique, the present inventors found that there is a problem of leakage of liquid from a suction device body when the irrigation function-equipped suction device is used.

In particular, upon occurrence of leakage of liquid from the suction device body, the liquid leaked during suction is discharged to the outside of the irrigation function-equipped suction device through a suction path, and thus, the prepared liquid is substantially consumed beyond an estimated amount of use.

In order to solve the program of liquid leakage, the present inventors have addressed the problem of liquid leakage by studying improvement of the irrigation function-equipped suction device and installing rubber packing at a part from which liquid is leaked.

However, despite considerable repetition of trial and error for improvement, unfortunately, none of structures of conventionally known irrigation function-equipped suction devices has solved the problem of liquid leakage to this date.

An object of the present invention is to provide an irrigation function-equipped suction device that prevents liquid leakage.

Solution to Problem

If liquid leaks from a movable member, it is normal to study a countermeasure for the movable member itself, from which liquid leaks.

After a great deal of diligent study to solve the aforementioned problem, the present inventors have conceived of a revolutionary idea of installing a closing valve upstream in an irrigation path of an irrigation function-equipped suction device. Here, upstream in an irrigation path refers to the side of the irrigation path, from which of liquid flows into a suction device body.

The present inventors have found that if a closing valve is installed upstream in an irrigation path, upon the irrigation path being closed, it is possible to prevent liquid pressure from being applied to respective mechanisms inside the suction device body, the mechanisms being located downstream of the closing valve. In addition, a first switch mechanism that switches between communication and closing of a suction path is provided in a first section, and a conversion mechanism that converts opening/closing motion of a rotation lever into linear motion along a longitudinal direction of the irrigation path is provided in a second section, enabling, even if leakage of liquid occurs during operation of the conversion mechanism that is in contact with the irrigation path, a path of direct travel of the leaked liquid from the second section to the first section to be closed off.

The present inventors have found that if the respective mechanisms are provided separately in the first section and the second section, liquid leaked from the conversion mechanism, which easily causes liquid leakage, can be prevented from being endlessly continuously sucked to the suction path side and thus have completed the present invention.

Specifically, the present invention provides [1] An irrigation function-equipped suction device including:
a suction device body;
a rotation lever provided so as to be capable of being opened or closed relative to the suction device body;
a suction path provided in the suction device body;
an irrigation path provided in the suction device body;
a flexible tube having a proximal end attached to a distal end of the suction device body, a distal end of the flexible tube being directed to a surgical site;

a first switch mechanism including a rotation valve, the first switch mechanism making switching to cause the suction path and the flexible tube to communicate with each other or be closed off from each other;

a second switch mechanism including a closing valve, the second switch mechanism making switching to cause the irrigation path and the flexible tube to communicate with each other or be closed off from each other; and a conversion mechanism that causes opening/closing motion of the rotation lever to be converted into linear motion along a longitudinal direction of the irrigation path by rotational motion of a rotation drum to move the closing valve, wherein:

if the suction path and the flexible tube are brought into communication with each other by the first switch mechanism, the irrigation path is closed by the second switch mechanism and the conversion mechanism;

if the suction path is closed by the first switch mechanism, the irrigation path and the flexible tube are brought into communication with each other by the second switch mechanism and the conversion mechanism;

the first switch mechanism is provided in a first section inside the suction device body;

the second switch mechanism and the conversion mechanism are provided in a second section inside the suction device body;

an irrigation path internal joining member included in the conversion mechanism, the irrigation path internal joining member making linear motion along the longitudinal direction of the irrigation path, is provided inside the irrigation path;

the irrigation path is connected to the suction path at a position on the flexible tube side relative to the rotation valve included in the first switch mechanism and the rotation drum included in the conversion mechanism, based on a plane perpendicular to a linear line along the longitudinal direction of the irrigation path; and the closing valve included in the second switch mechanism is disposed at a position on a side opposite to the flexible tube relative to the rotation valve included in the first switch mechanism and the rotation drum included in the conversion mechanism, based on the plane perpendicular to the linear line along the longitudinal direction of the irrigation path.

Also, an aspect of the present invention provides [2] The irrigation function-equipped suction device according to [1] above, wherein if the irrigation path is closed by the second switch mechanism, a path for communication with atmosphere is kept for the conversion mechanism.

Also, an aspect of the present invention provides [3] The irrigation function-equipped suction device according to [1] or [2] above, wherein:

the second switch mechanism includes the closing valve that closes the irrigation path, and the irrigation path internal joining member that makes linear motion along the longitudinal direction of the irrigation path relative to the closing valve, along with an operation of the conversion mechanism; and wherein the rotation drum controls movement and stoppage of the closing valve during the linear motion of the irrigation path internal joining member.

Also, an aspect of the present invention provides [4] The irrigation function-equipped suction device according to any of [1] to [3] above, including:

a first opening/closing joining member and a second opening/closing joining member each movably joined to the rotation lever;

a first rotation joining member movably joined to the first opening/closing joining member, the rotation valve being movably joined to the first rotation joining member; and a second rotation joining member movably joined to the second opening/closing joining member, the rotation drum being movably joined to the second rotation joining member;

wherein:

the irrigation path internal joining member is movably joined to the rotation drum, along with an operation of insertion of the first opening/closing joining member to the first section, the rotation valve rotates and thereby closes the suction path, along with an operation of insertion of the second opening/closing joining member to the second section, the rotation drum rotates and thereby brings the irrigation path into communication, subsequent to the closing of the suction path, the irrigation path is brought into communication, along with an operation of the first opening/closing joining member being pulled out from the first section, the rotation valve rotates and thereby brings the suction path into communication, along with an operation of the second opening/closing joining member being pulled out from the second section, the rotation drum rotates and thereby closes the irrigation path, and subsequent to the closing of the irrigation path, the suction path is brought into communication are provided.

Also, an aspect of the present invention provides [5] The irrigation function-equipped suction device according to any of [1] to [4] above, wherein:

the irrigation path internal joining member includes a closing valve push-out portion and a closing valve pull-back portion;

the closing valve includes a closing portion, an open side surface and an irrigation path internal joining member contact portion;

the closing valve push-out portion and the closing valve pull-back portion are provided in the irrigation path internal joining member in such a manner that the closing valve push-out portion and the closing valve pull-back portion are spaced from each other;

if the irrigation path internal joining member moves to a side of the suction device body opposite to a flexible tube-provided side of the suction device body, the closing valve push-out portion of the irrigation path internal joining member comes into contact with the irrigation path internal joining member contact portion of the closing valve, the closing valve is pushed out to the side of the suction device body opposite to the flexible tube-provided side of the suction device body, closing of the irrigation path by the closing valve is cancelled, and the open side surface of the closing valve is exposed inside a part of the irrigation path on the side of the suction device body opposite to the flexible tube-provided side of the suction device body and the irrigation path is thereby brought into communication, and if the irrigation path internal joining member moves to the flexible tube-provided side of the suction device body, the closing valve pull-back portion of the irrigation path internal joining member comes into contact with the irrigation path internal joining member contact portion of the closing valve, the closing valve is pulled back to the flexible tube-provided side of the suction device body and the irrigation path is closed by the closing valve.

Also, an aspect of the present invention provides [6] The irrigation function-equipped suction device according to any of [1] to [5] above, wherein:

the closing valve is pressed to the suction device body side from the outer side of the suction device body by a repulsive force of an elastic body, during linear motion of the irrigation path internal joining member, if there is a space between the closing valve push-out portion of the irrigation path internal joining member and the irrigation path internal joining member contact portion of the closing valve, the closing valve keeps closing the irrigation path.

Also, an aspect of the present invention provides [7] The irrigation function-equipped suction device according to any of [1] to [6] above, wherein:

the rotation lever includes a depression portion, an adjustment hole and a conduction path that brings the rotation lever into communication, the adjustment hole is provided in the depression portion in an outer surface of the rotation lever, an end of the conduction path is connected to the adjustment hole, and another end of the conduction path is connected to the suction path via the flexible tube.

Also, an aspect of the present invention provides [8] The irrigation function-equipped suction device according to [4] above, wherein:

each of the first opening/closing joining member and the second opening/closing joining member includes an opening/closing joining member body portion and a curve surface portion provided at each of opposite ends of both of the opening/closing joining member body portions, and based on a cross-section perpendicular to a longitudinal direction of the opening/closing joining member body portion, a largest cross-section of each of the curve surface portions is larger than a largest cross-section of the opening/closing joining member body portion, and as observed in the longitudinal direction of the opening/closing joining member body portion, the largest cross-section of the opening/closing joining member body portion is located within the largest cross-section of each of the curve surface portions.

Also, an aspect of the present invention provides [9] The irrigation function-equipped suction device according to [1] or [4] above, wherein:

the rotation valve includes a hollow portion, a void provided inside the rotation valve, and a vent hole that makes the void and an outside of the rotation valve communicate with each other, neither the void nor the vent hole communicates with the hollow portion inside the rotation valve, and when the suction path and the flexible tube are closed off from each other, the vent hole is exposed in the suction path.

Advantageous Effects of Invention

Like in the conventional techniques, where a conventional switch mechanism that controls whether a suction path and a flexible tube communicate with each other or are closed off from each other and a conventional switch mechanism that controls whether an irrigation path and the flexible tube communicate with each other or are closed off from each other are provided in a same section, if leakage of liquid from the conventional switch mechanism that controls whether the irrigation path and the flexible tube communicate with each other or are closed off from each other occurs, the leaked liquid is endlessly continuously sucked into the suction path, resulting in a waste of a large amount of liquid necessary for, e.g., brain surgery.

On the other hand, in the case of the irrigation function-equipped suction device according to the present invention, a switch mechanism that controls whether the irrigation path and the flexible tube communicate with each other or closed off from each other and a conversion mechanism that converts opening/closing motion of the rotation lever into linear motion along the longitudinal direction of the irrigation path are not provided in a section that is the same as a switch mechanism that controls whether the suction path and the flexible tube communicate with each other or are closed off from each other.

Therefore, even if leakage of liquid occurs in the switch mechanism that controls whether the irrigation path and the flexible tube communicate with each other or are closed off from each other, the leaked liquid can be prevented from being directly sucked into the suction path.

Also, as in the conventional techniques, in the case of a structure that controls communication and closing of an irrigation path subjected to water pressure by a rotation valve or a structure that controls communication and closing of an irrigation path subjected to water pressure by vertically moving a conduction path between a suction path and the irrigation path via a piston valve, each of movable members need to have a watertight structure.

However, if the watertight structure is provided by enhancing precision of machining of each movable member and thereby maximally reducing a gap formed by the movable member or the watertight structure is provided by disposing a water leakage prevention member around the movable members, a smooth driving operation of the movable members is hindered.

In such a case, it is extremely difficult for a surgeon to stop a rotation lever at an arbitrary position to make fine adjustment of an amount of suction and an amount of irrigation.

On the other hand, in the case of the irrigation function-equipped suction device according to the present invention, the closing valve included in the second switch mechanism that controls communication and closing of the irrigation path subjected to liquid pressure is disposed upstream in the irrigation path, that is, at a position on the side opposite to the flexible tube relative to the first switch mechanism and the conversion mechanism in the suction device body.

When the irrigation path is closed, the closing valve included in the second switch mechanism blocks a liquid flow to the first switch mechanism and the conversion mechanism upstream in the irrigation path.

As a result, even if the irrigation path is closed, the first switch mechanism and the conversion mechanism can be prevented from being subjected to liquid pressure.

Therefore, when the irrigation path is closed, leakage of liquid from the movable members in the present invention can be prevented.

Also, in the case of the irrigation function-equipped suction device according to the present invention, the irrigation path is connected to the suction path at a position downstream of each of the first switch mechanism and the conversion mechanism.

When liquid flows as a result of the irrigation path and the flexible tube being brought into communication with each other, the liquid is discharged to the outside from the one end side of the flexible tube, and thus, application of excessive liquid pressure to the first switch mechanism located in the suction path and the conversion mechanism can be reduced, enabling prevention of liquid leakage from the first switch mechanism.

Next, in the irrigation function-equipped suction device according to the present invention, if the suction path and the flexible tube are brought into communication with each other and the irrigation path is closed by the closing valve, a communication path from the closing valve to the end of the flexible tube through the connection portion of the suction path is formed.

Since the end of the flexible tube communicates with atmosphere, after the irrigation path is closed by the closing valve, no liquid pressure is substantially applied to the conversion mechanism and the second switch mechanism that are in contact with the irrigation path, enabling prevention of liquid leakage from the suction device body.

Next, in the irrigation function-equipped suction device according to the present invention, during linear motion of the irrigation path internal joining member, it is possible to make switching to cause the closing valve to be moved or stopped.

Even if the irrigation path internal joining member makes linear motion inside the irrigation path according to a closing operation of the rotation lever, the closing valve can be kept at a position at which the irrigation path is closed until the suction path is closed.

DESCRIPTION OF EMBODIMENTS

Embodiment 1 of Invention

An embodiment of the present invention will be described below with reference to the drawings.

Figure 1:
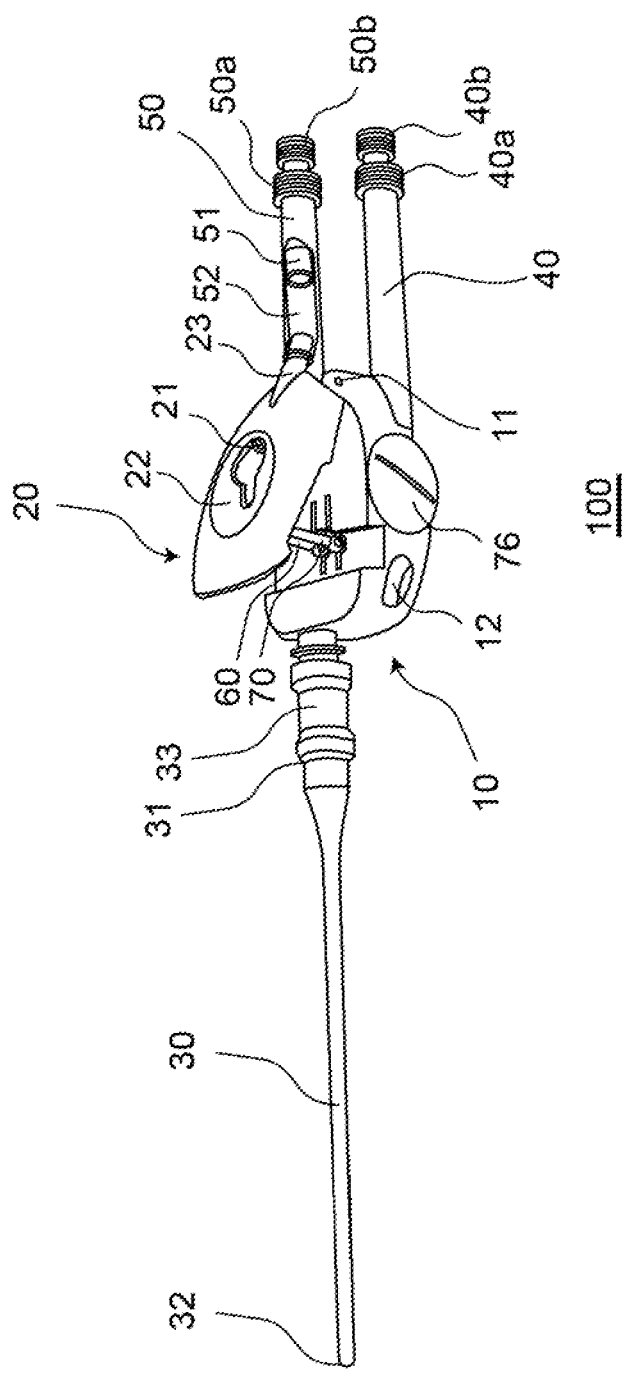
FIG. 1 is a schematic perspective view for describing an irrigation function-equipped suction device 100 according to Embodiment 1.

FIG. 1 is a schematic perspective view for describing an irrigation function-equipped suction device 100 according to Embodiment 1.

Figure 2:
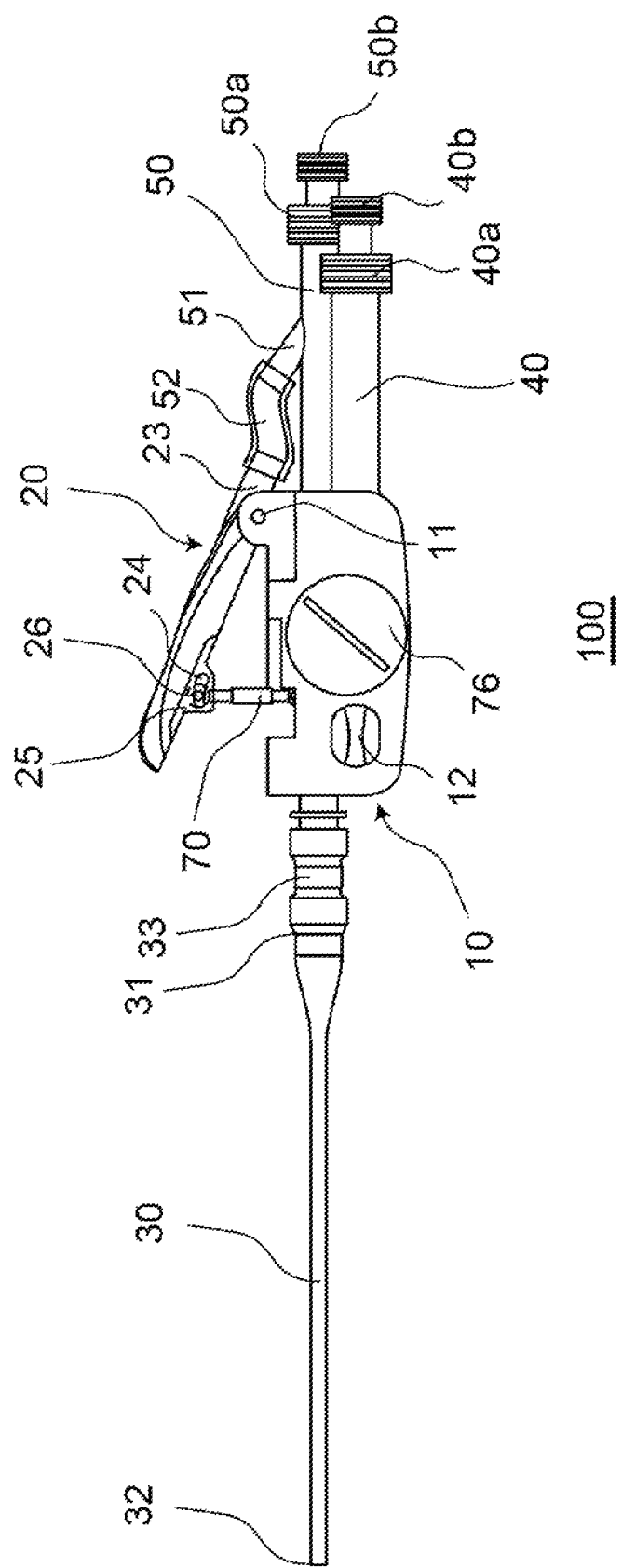
FIG. 2 is a schematic side view for describing the irrigation function-equipped suction device 100 according to Embodiment 1.
Figure 3:
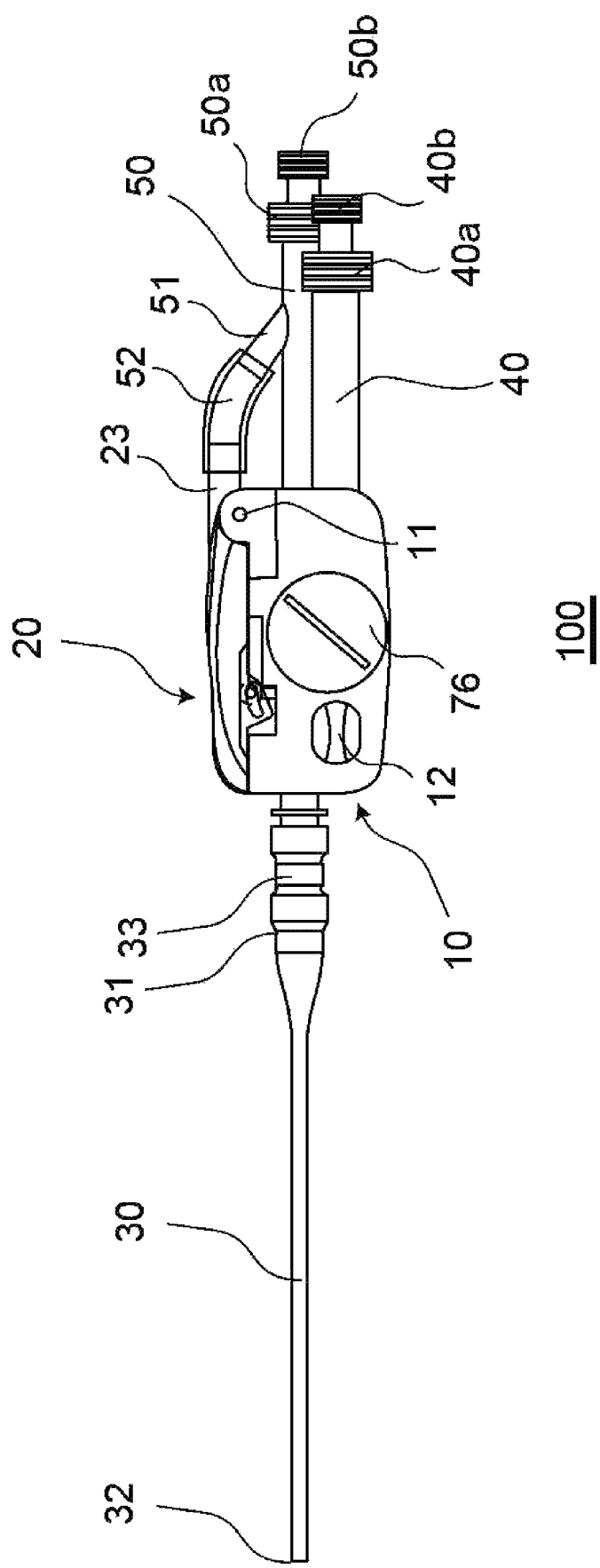
FIG. 3 is a schematic side view for describing the irrigation function-equipped suction device 100 according to Embodiment 1.

Also, FIGS. 2 and 3 are schematic side views for describing the irrigation function-equipped suction device 100 according to Embodiment 1.

In the irrigation function-equipped suction device 100 according to Embodiment 1 of the present invention, a rotation lever 20 is joined to a suction device body 10 by an opening/closing connection portion 11 so as to be capable of being opened or closed. Elastic repulsive means 15 such as torsion springs (see FIG. 5) are provided between the suction device body 10 and the rotation lever 20 and the rotation lever 20 can be kept in an open state by the elastic repulsive means 15.

FIGS. 1 and 2 illustrate the rotation lever 20 in an open state and FIG. 3 illustrates the rotation lever 20 closed by a maneuver to apply an external force to the rotation lever 20 such as pressing the rotation lever 20 with a finger.

A flexible tube 30 including a proximal end 31 attached to a suction device body 10 and a distal end 32 to be directed to a surgical site, wherein the flexible tube 30 is detachably connected to the suction device body 10 via a connection tube 33.

The flexible tube 30 is hollow inside, enabling, e.g., liquid or gas to freely travel through the inside thereof.

Furthermore, the flexible tube 30 can freely be bent and can be kept in a certain shape resulting from being bent. Note that although an opening portion is provided at the distal end 32 of the flexible tube 30 illustrated in FIGS. 1 to 3, the opening portion may be provided in a side surface of the flexible tube 30.

Also, the flexible tube 30 can be replaced with, e.g., one with a large tube diameter or one with a small tube diameter depending on the purpose.

In the suction device body 10, a depression portion 12 is provided as a point a finger is put on when the irrigation function-equipped suction device 100 is held.

The installation of the depression portion 12 enables the irrigation function-equipped suction device 100 to be easily held and thus facilitates keeping the flexible tube 30 at a fixed position.

An irrigation tube 40 and a suction tube 50 are respectively connected to the suction device body 10.

In the irrigation tube 40, irrigation connection portions 40a, 40b for connecting an irrigation flexible tube (not illustrated) are provided.

At least one kind of liquid from among, e.g., water, distilled water, sterilized water, saline and drug solution can be introduced to the suction device body 10 through the irrigation flexible tube and the irrigation tube 40.

Examples of means for introducing the liquid to the suction device body 10 include means of holding a liquid container, to which the irrigation flexible tube is connected, at a position higher than the irrigation function-equipped suction device 100 and means of feeding liquid via the irrigation flexible tube using, e.g., a liquid feeding pump.

Likewise, in the suction tube 50, suction connection portions 50a, 50b for connecting a suction flexible tube (not illustrated) are provided.

Examples of means for introducing a suction function to the suction device body 10 include means of connecting a suction pump to the suction flexible tube.

In the rotation lever 20, a depression portion 22 including an adjustment hole 21 is provided. Furthermore, in the rotation lever 20, a hollow conduction path that makes a conduction tube 23 and the adjustment hole 21 communicate with each other is provided.

The conduction tube 23 communicates with a branch tube 51 provided in the suction tube 50, through a connection flexible tube 52 formed of a synthetic resin.

When the rotation lever 20 is not pressed and the adjustment hole 21 is not closed by a finger, the adjustment hole 21 and the suction tube 50 communicates with each other, enabling decrease of a suction force on the distal end 32 side of the flexible tube 30.

On the other hand, putting a finger on the depression portion 22 to close the adjustment hole 21 enables increase of the suction force on the distal end 32 side of the flexible tube 30.

Figure 4:
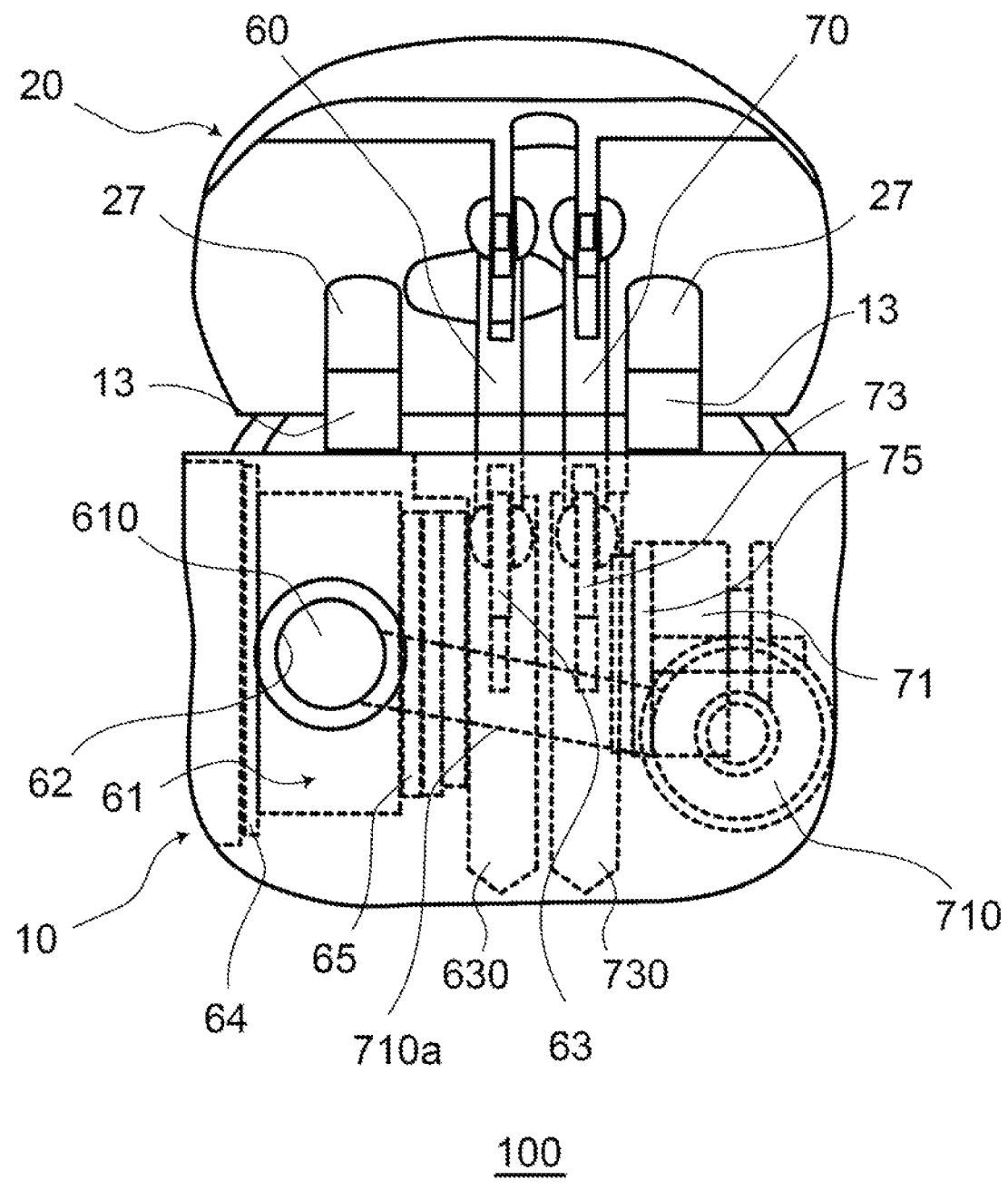
FIG. 4 is a schematic partial front view for describing the irrigation function-equipped suction device 100 according to Embodiment 1.

FIG. 4 is a schematic partial front view for describing the irrigation function-equipped suction device 100 according to Embodiment 1. Also, FIG. 5 is a schematic back perspective view for describing the irrigation function-equipped suction device 100 according to Embodiment 1.

Figure 5:
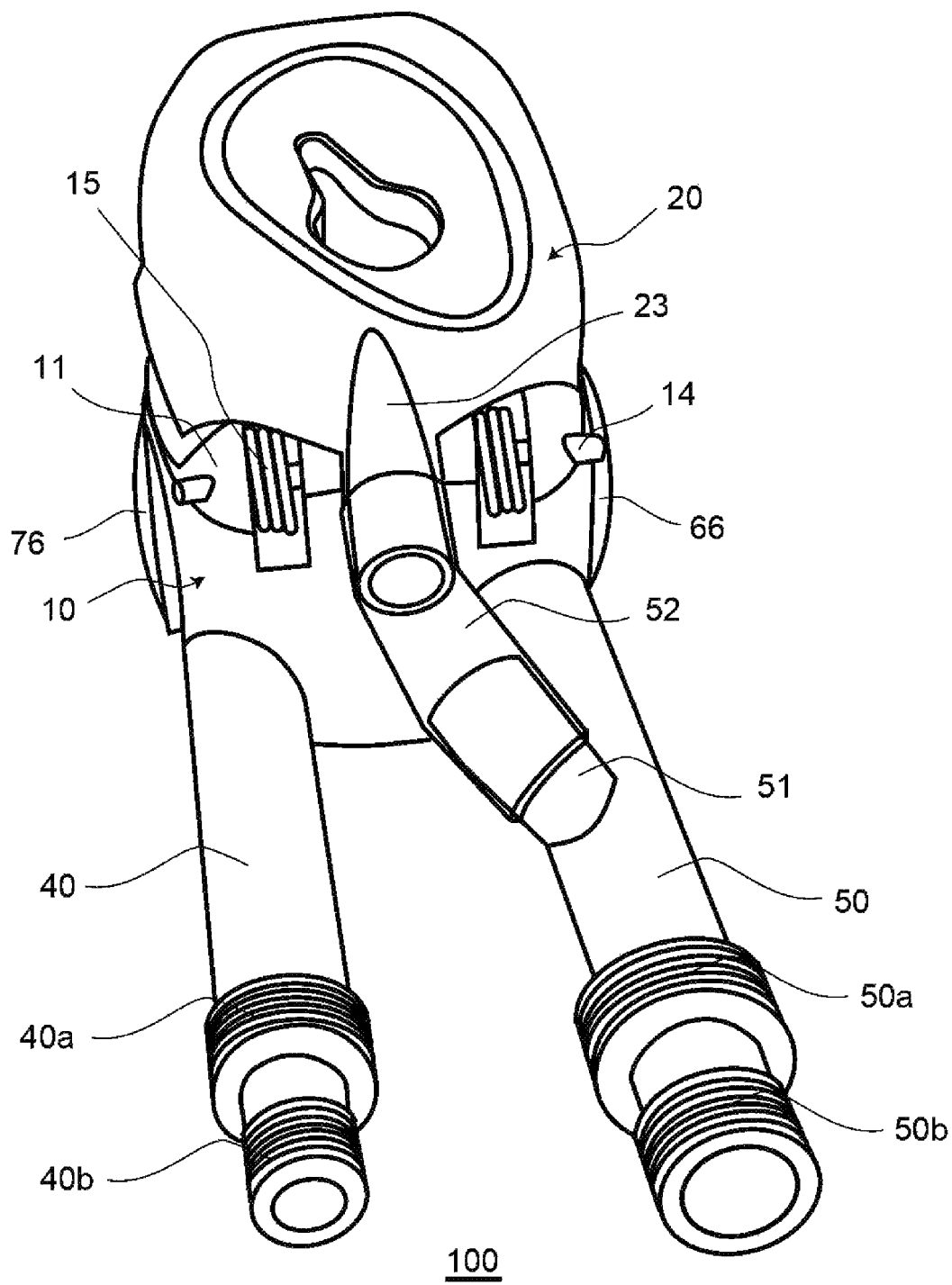
FIG. 5 is a schematic back perspective view for describing the irrigation function-equipped suction device 100 according to Embodiment 1.

FIG. 4 is a diagram of the irrigation function-equipped suction device 100 as observed from the flexible tube 30-provided side and FIG. 5 is a diagram of the irrigation function-equipped suction device 100 as observed from the side opposite to the flexible tube 30-provided side.

A first opening/closing joining member 60 and a second opening/closing joining member 70 are each movably joined to the rotation lever 20.

Upon opening/closing of the rotation lever 20, the first opening/closing joining member 60 and the second opening/closing joining member 70 each move vertically according to the degree of the opening/closing of the rotation lever 20 as illustrated in FIGS. 1 to 3.

In the rotation lever 20, protrusion portions 25 each including an elongated hole 24 are provided (see FIG. 2). The first opening/closing joining member 60 is provided so as to pinch a protrusion portion 25 from opposite sides. A screw 26 penetrates through the first opening/closing joining member 60 and the elongated hole 24 and the first opening/closing joining member 60 and the elongated hole 24 are thereby movably joined to each other.

The same applies to a structure of the second opening/closing joining member 70 and the rotation lever 20.

As illustrated in FIG. 5, the suction device body 10 and the rotation lever 20 are movably joined to each other via a joining long pivot shaft pin 14.

Joining portions 13, 13 provided in the suction device body 10 are housed in respective groove portions 27, 27 of the rotation lever 20 when the rotation lever 20 is closed.

Figure 6:
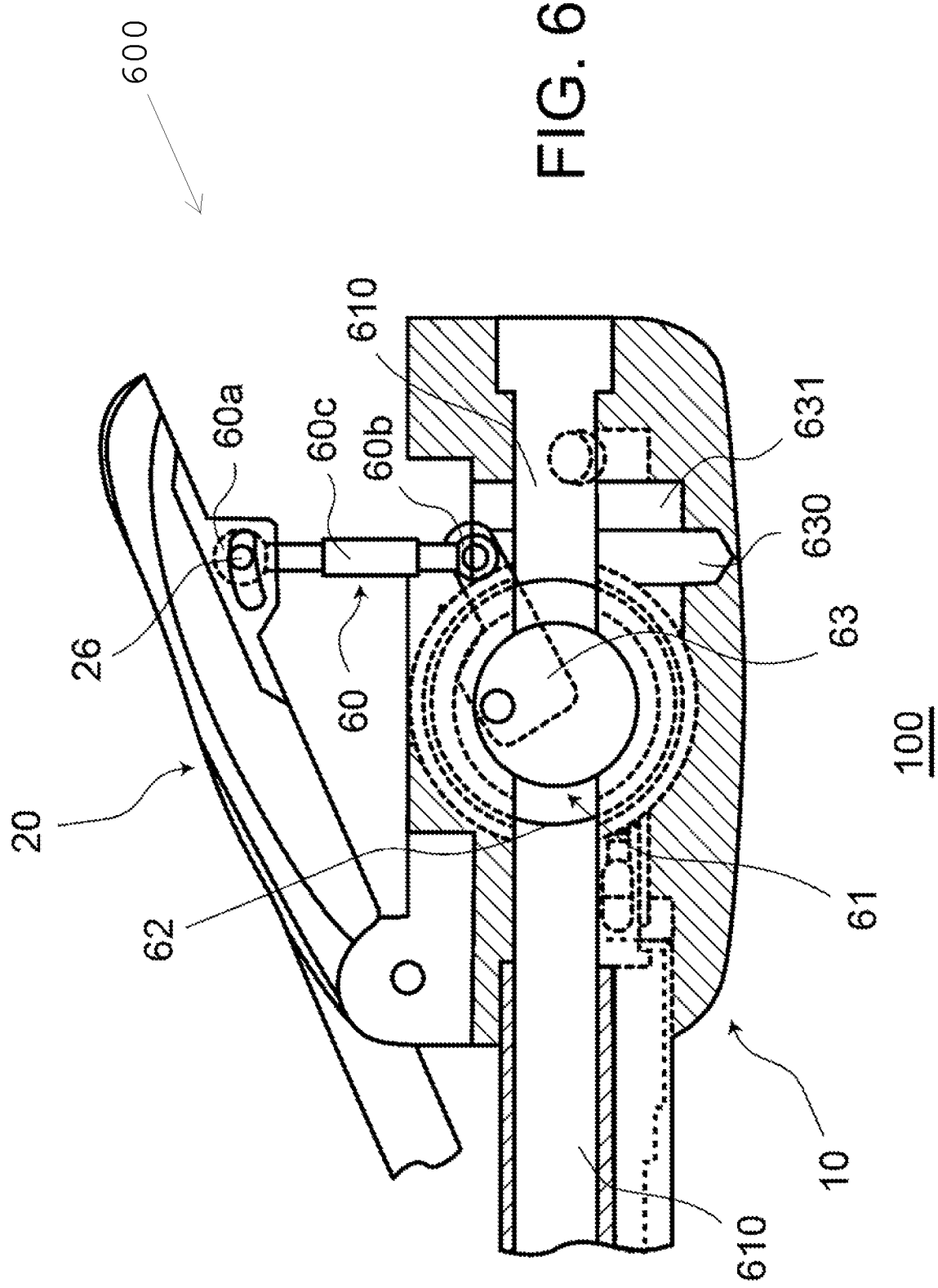
FIG. 6 is a schematic partial sectional view for describing a first switch mechanism that makes a suction path and a flexible tube communicate with each other.
Figure 7:
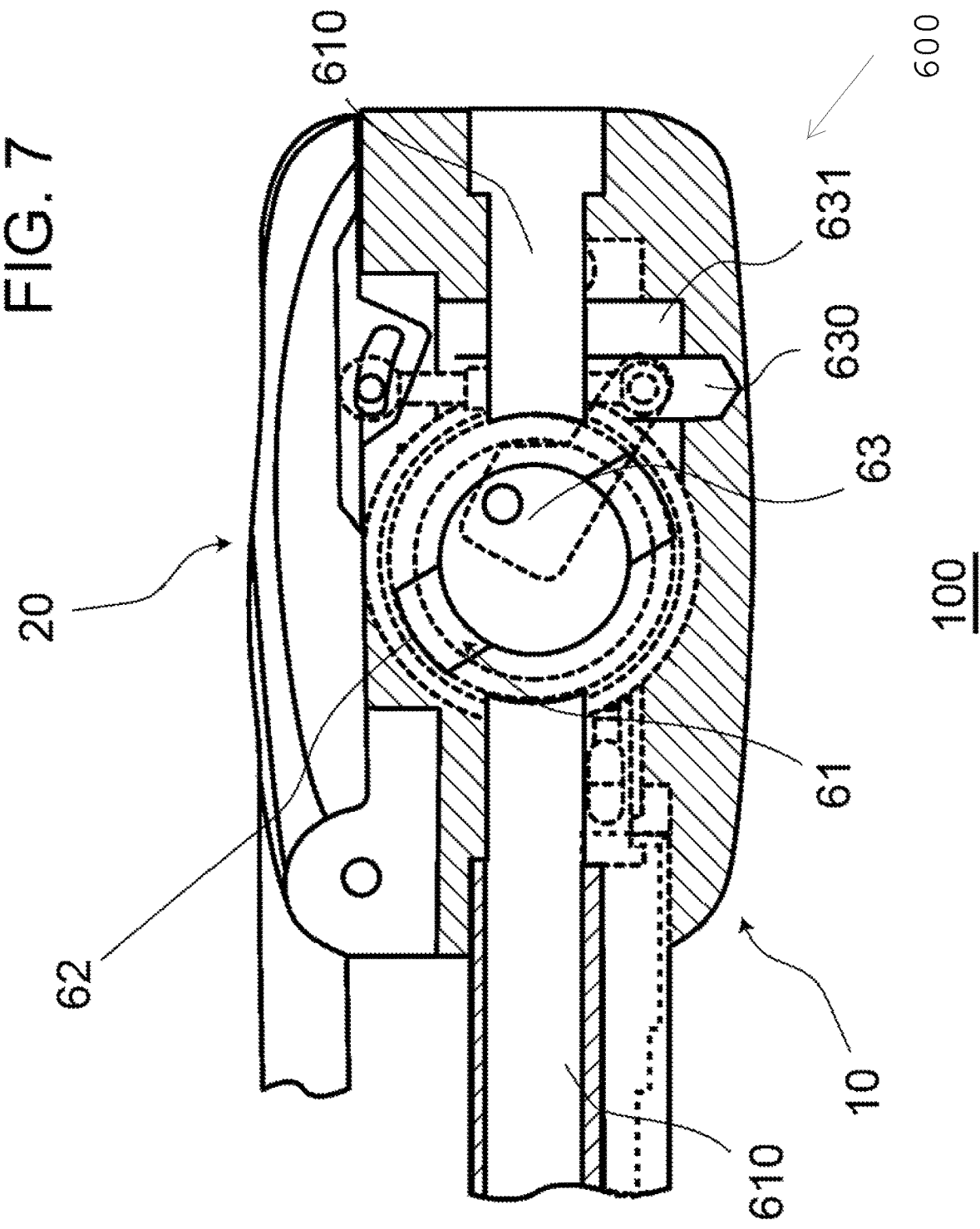
FIG. 7 is a schematic partial sectional view for describing the first switch mechanism that makes a suction path and a flexible tube be closed off from each other.

FIGS. 6 and 7 are schematic partial sectional views for describing a first switch mechanism that makes switching to cause a suction path and the flexible tube to communicate with each other or be closed off from each other.

Figure 8:
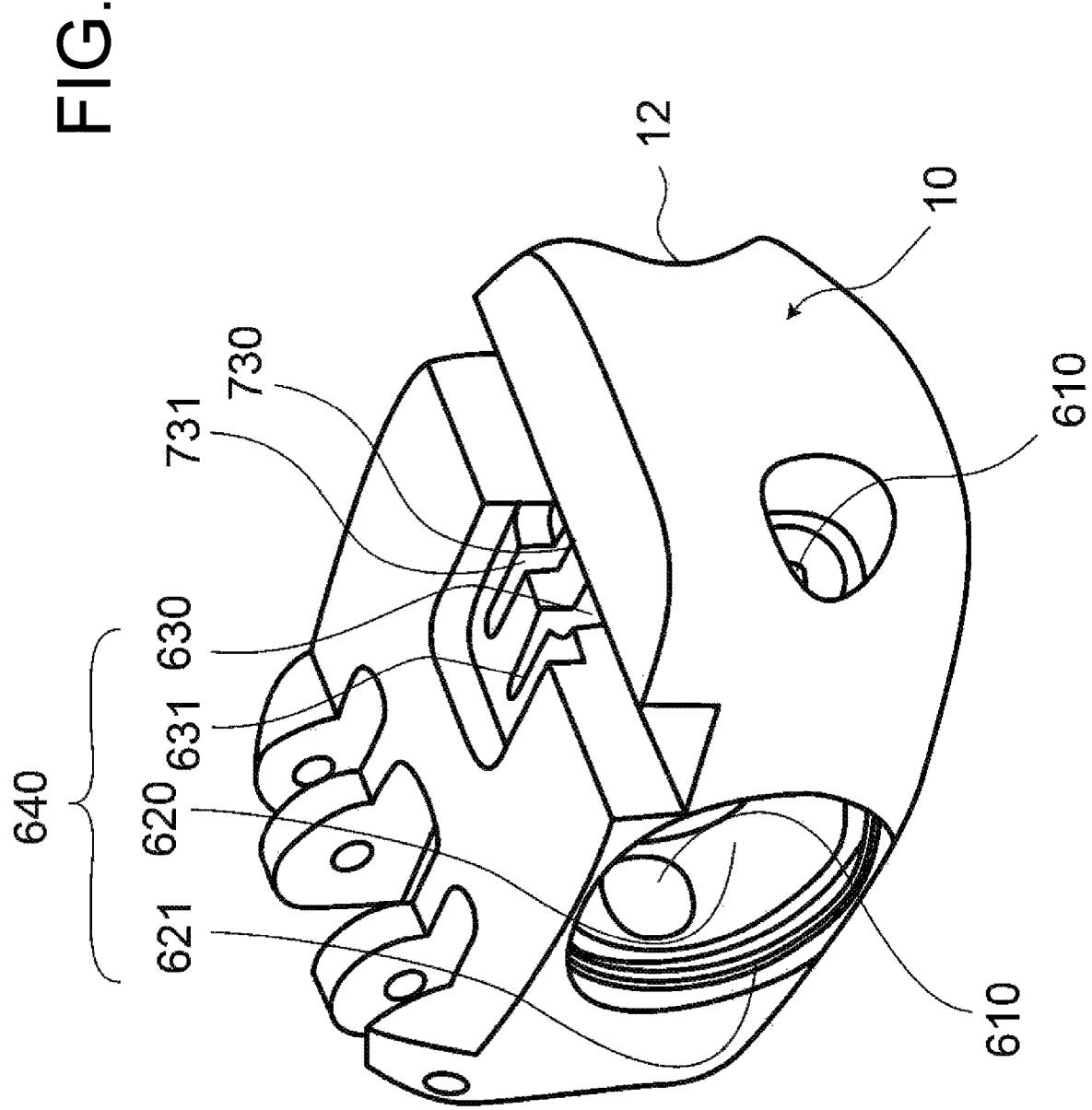
FIG. 8 is a schematic perspective view illustrating a suction device body as viewed from the flexible tube-provided side.

FIG. 8 is a schematic perspective view illustrating the suction device body as viewed from the flexible tube-provided side.

A first switch mechanism 600 includes a rotation valve 61. The rotation valve 61 includes a cylindrical hollow portion 62 incorporated therein.

Rotation of the rotation valve 61 enables the suction path 610 and the hollow portion 62 to communicate with each other or be closed off from each other.

The rotation valve 61 can be rotatably inserted onto a hollow inner surface of a hollow cavity 620 provided inside the suction device body 10, with substantially no gap therebetween.

"With substantially no gap" here means that when the rotation valve 61 is inserted to the hollow cavity 620, no light transmitted from an interface of contact between the rotation valve 61 and the hollow cavity 620 (see FIG. 8) is visible to the naked eye but the rotation valve 61 is rotatable.

Preferably, a part of an outer circumferential surface of the rotation valve 61 is in contact with the hollow inner surface of the hollow cavity 620, and more preferably, an entirety of the outer circumferential surface of the rotation valve 61 is in contact with the hollow inner surface of the hollow cavity 620.

Rotation of the rotation valve 61 inside the hollow cavity 620 enables the hollow portion 62 of the rotation valve 61 and the suction path 610 to communicate with each other or be closed off from each other.

As illustrated in FIG. 6, when the rotation lever 20 is open, that is, when no external force is applied to the rotation lever 20, the hollow portion 62 of the rotation valve 61 provided in a first section 640 (see FIG. 8) inside the suction device body 10 communicates with the suction path 610.

The suction path 610 linearly extends through the suction device body 10 and the rotation valve 61 is provided among the suction path 610.

Upon the rotation lever 20 being pressed with, e.g., a finger of a surgeon, the first opening/closing joining member 60 is pressed down. A first rotation joining member 63 is movably joined to the first opening/closing joining member 60.

As a result of the first opening/closing joining member 60 being pressed down, the first rotation joining member 63 moves. The movement is transmitted from the first rotation joining member 63 to the rotation valve 61, whereby the rotation valve 61 rotates and the hollow portion 62 provided inside the rotation valve 61 is closed.

On the other hand, upon the force pressing the rotation lever 20 being lessened, the rotation lever 20 and the suction device body 10 are opened from each other by means of an action of the elastic repulsive means 15 such as torsion springs (see FIG. 5) and the rotation valve 61 rotates reversely, whereby the hollow portion 62 provided inside the rotation valve 61 communicates with the suction path 610.

Preferably, the hollow portion 62 inside the rotation valve 61 and the suction path 610 are disposed linearly and respective sections in a longitudinal direction of the hollow portion 62 and the suction path 610 are constant and match with each other in the longitudinal direction.

Preferably, when the hollow portion 62 inside the rotation valve 61 and the suction path 610 completely communicate with each other, the hollow portion 62 inside the rotation valve 61 and the suction path 610 form a path with no irregularities inside.

Since foreign substances such as bone fragments sucked from the flexible tube 30 smoothly travel through the path, the inside of the suction path 610 can be prevented from being occluded by the foreign substances inside the irrigation function-equipped suction device 100.

Each of respective sectional shapes in a direction perpendicular to the longitudinal direction of the hollow portion 62 inside the rotation valve 61 and the suction path 610 is formed preferably by a smooth curve such as a circle or an ellipse, more preferably by a circle.

As illustrated in FIG. 8, in the suction device body 10, the suction path 610 is provided linearly through the suction device body 10. The hollow cavity 620 for inserting the rotation valve 61 is provided at an intermediate position in the suction path 610.

In the suction device body 10, a first opening/closing joining member insertion hole 630 for inserting the first opening/closing joining member 60 from the upper side in FIG. 8 is provided.

Also, in the suction device body 10, a first rotation joining member installation groove 631 for movably housing the first rotation joining member 63 is provided.

The hollow cavity 620, the first opening/closing joining member insertion hole 630 and the first opening/closing joining member insertion groove 631 form the first section 640.

The first opening/closing joining member 60 is inserted to the first section 640 so as to be movable in the vertical direction in FIGS. 6 and 7. The first opening/closing joining member 60 is movably joined to the first rotation joining member 63. Also, the first rotation joining member 63 is movably joined to the rotation valve 61.

Annular elastic bodies 64, 65 such as O-rings are disposed on opposite sides of the rotation valve 61 (see FIG. 4). A cover body 66 (not illustrated) including a screw portion is screwed from the outside into a screw groove 621 (see FIG. 8) provided inside the hollow cavity 620.

As illustrated in FIG. 4, the annular elastic bodies 64, 65 such as O-rings are provided in an opening portion formed in a step-like shape inside the hollow cavity 620, and even if the cover body 66 presses the annular elastic bodies 64, 65 such as O-rings from the outside, the annular elastic bodies 64, 65 do not hinder rotation of the rotation valve 61.

Also, when liquid travels through the suction path 610, the annular elastic bodies 64, 65 such as O-rings close the opposite sides of the rotation valve 61, enabling the liquid to be prevented from being leaked from the first opening/closing joining member insertion hole 630 or the first rotation joining member installation groove 631.

Figure 9:
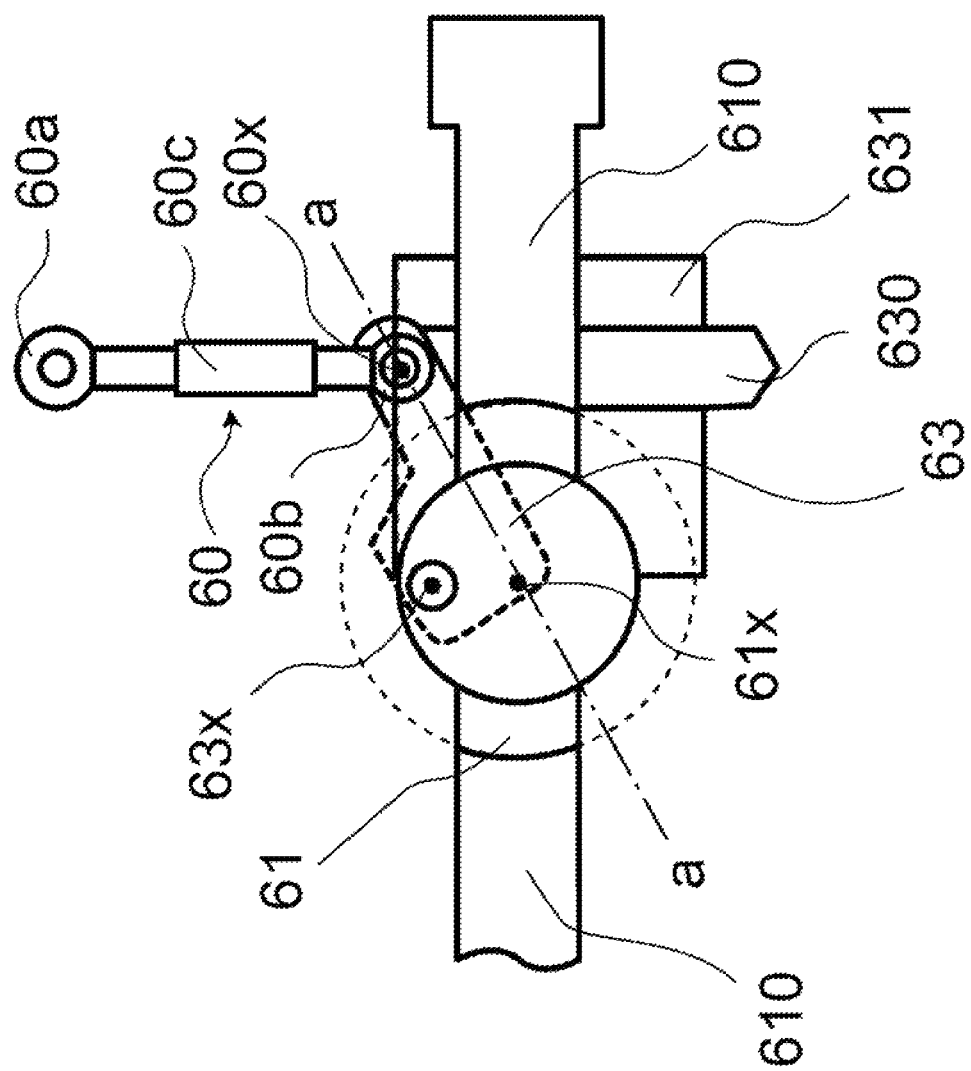
FIG. 9 is a schematic partial view for describing an interlocking relationship among a first opening/closing joining member, a first rotation joining member and a rotation valve.
Figure 10:
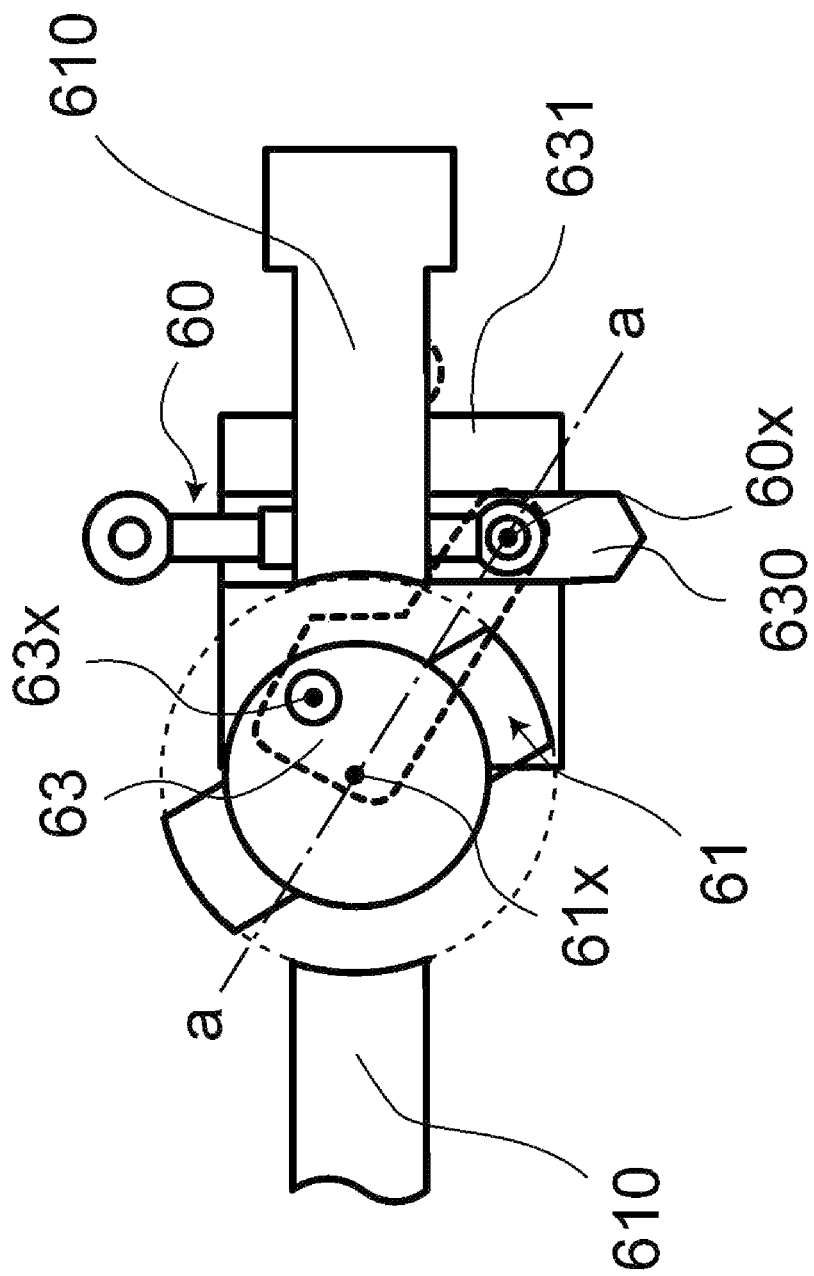
FIG. 10 is a schematic partial view for describing an interlocking relationship among the first opening/closing joining member, the first rotation joining member and the rotation valve.

FIGS. 9 and 10 are schematic partial views for describing an interlocking relationship among the first opening/closing joining member, the first rotation joining member and the rotation valve.

As illustrated in FIGS. 9 and 10, the first rotation joining member 63 and the rotation valve 61 are movably joined to each other at a position on the first opening/closing joining member 60 side relative to a straight line connecting a joining axle $60x$ between the first opening/closing joining member 60 and the first rotation joining member 63 and a center axis $61x$ of the rotation valve 61 (alternate long and short dash line a-a).

As described above, as a result of the first rotation joining member 63 and the rotation valve 61 being movably joined at a position on the first opening/closing joining member 60 side relative to the straight line connecting the joining axle $60x$ between the first opening/closing joining member 60 and the first rotation joining member 63 and the center axis $61x$ of the rotation valve, vertical motion of the first opening/closing joining member 60 is smoothly converted into rotational motion of the rotation valve 61.

The first opening/closing joining member 60 includes an opening/closing joining member body portion $60c$, and curve surface portions $60a$, $60b$ provided at opposite ends of the opening/closing joining member body portion $60c$.

Based on a cross-section perpendicular to a longitudinal direction of the opening/closing joining member body portion $60c$, that is, the vertical direction in FIGS. 9 and 10, a largest cross-section of each of the curve surface portions $60a$, $60b$ is larger than a largest cross-section of the opening/closing joining member body portion $60c$.

If there are a plurality of such cross-sections, the relevant largest cross-section is calculated based on the area of an inner surface of an outer circumference connecting the plurality of cross-sections so that the outer circumference is shortest.

Also, if there is a hollow portion in the cross-section, the relevant largest cross-section is calculated based on the area of an inner surface of an outer circumference of the cross-section. The same applies to the below.

As observed in the longitudinal direction of the opening/closing joining member body portion $60c$, the largest cross-section of the opening/closing joining member body portion $60c$ is located within each of the respective largest cross-sections of the curve surface portions $60a$, $60b$.

Provision of the curve surface portions $60a$, $60b$ allows the first opening/closing joining member 60 to smoothly move along the inside of the first opening/closing joining member insertion hole 630 provided inside the suction device body 10.

Figure 11:
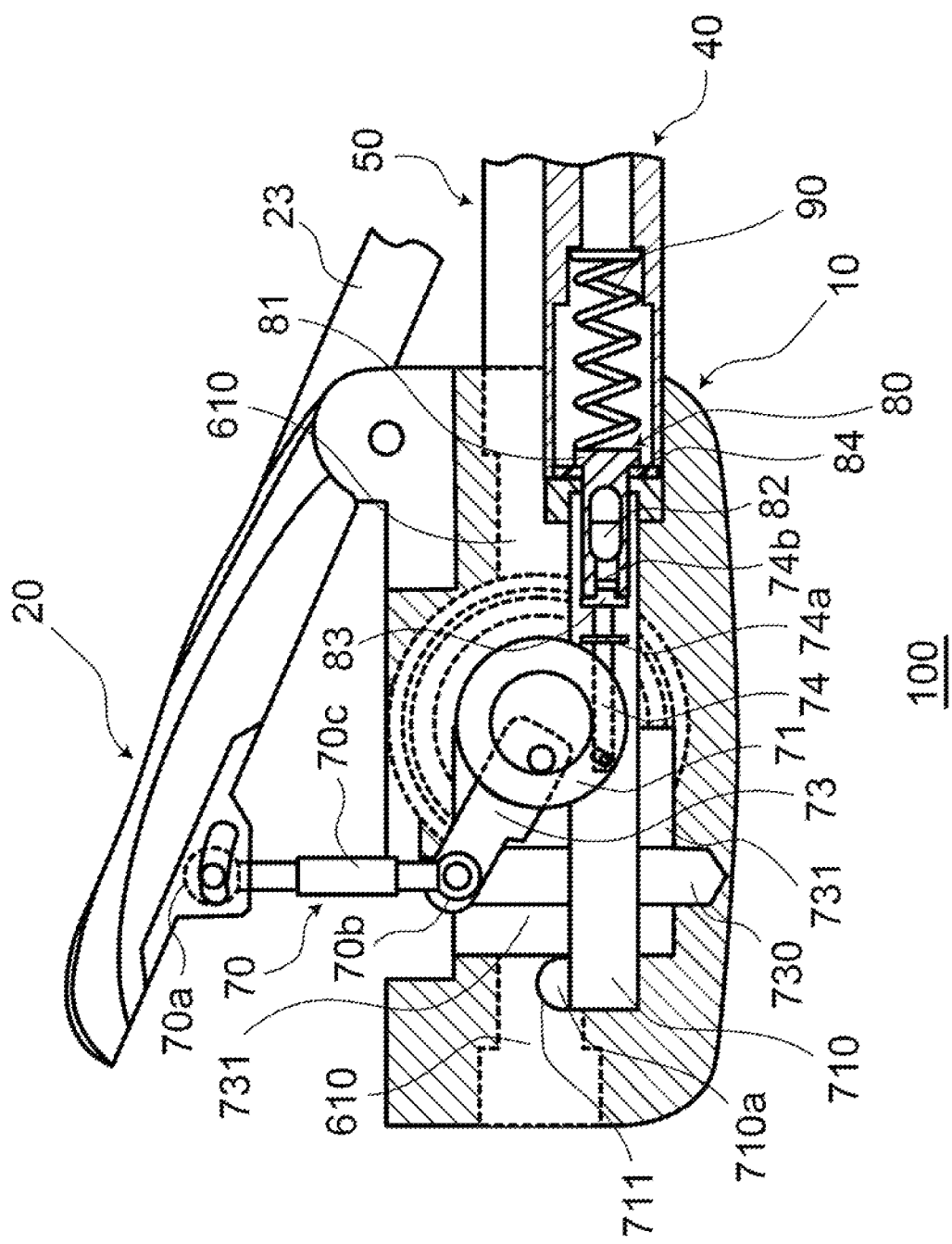
FIG. 11 is a schematic partial sectional view for describing a second switch mechanism when an irrigation path and the flexible tube are closed off from each other.
Figure 12:
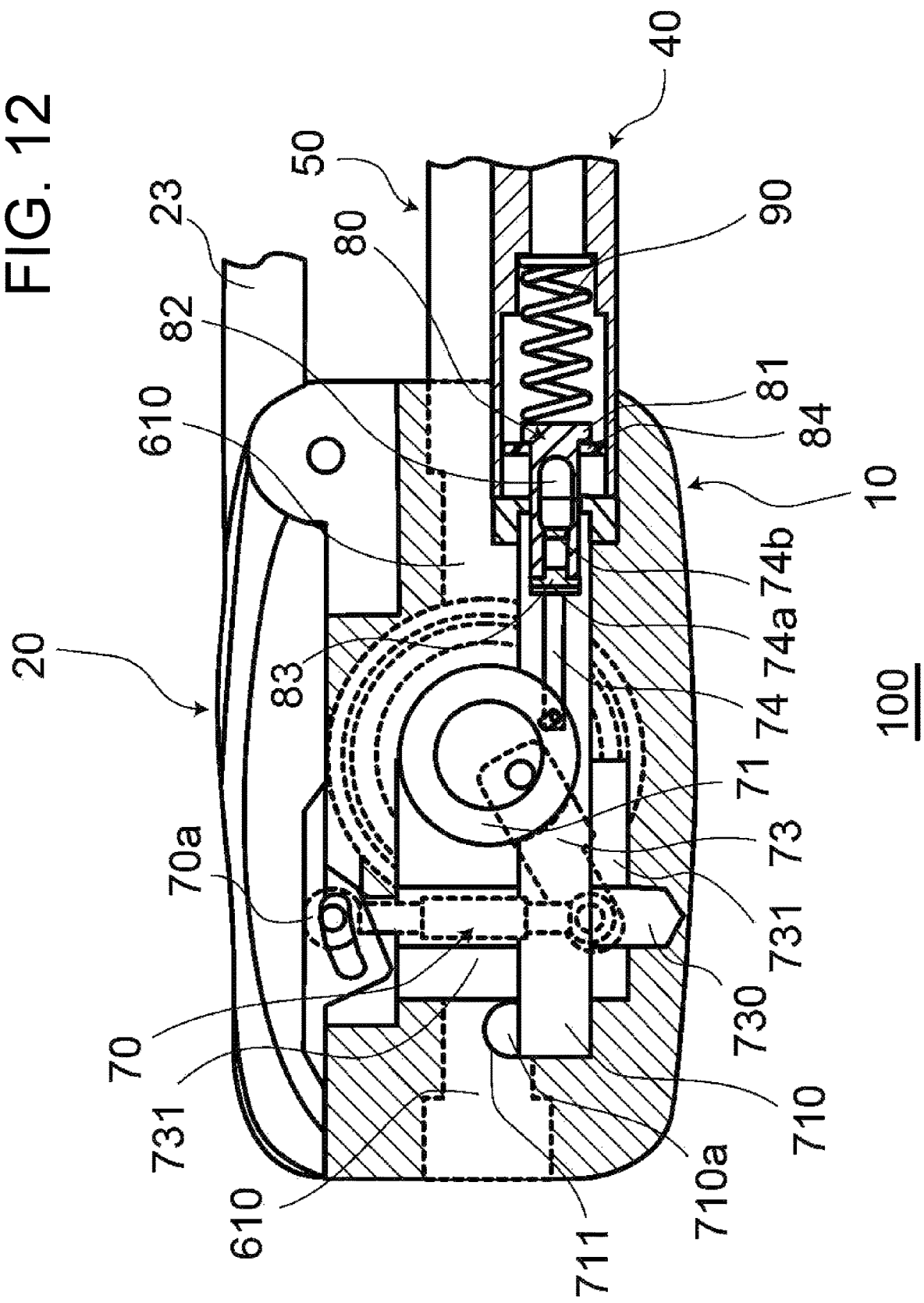
FIG. 12 is a schematic partial sectional view for describing the second switch mechanism when the irrigation path and the flexible tube communicate with each other.

FIGS. 11 and 12 are schematic sectional views for describing a second switch mechanism that makes switching to cause an irrigation path and a flexible tube to be closed off from each other or communicate with each other.

Figure 13:
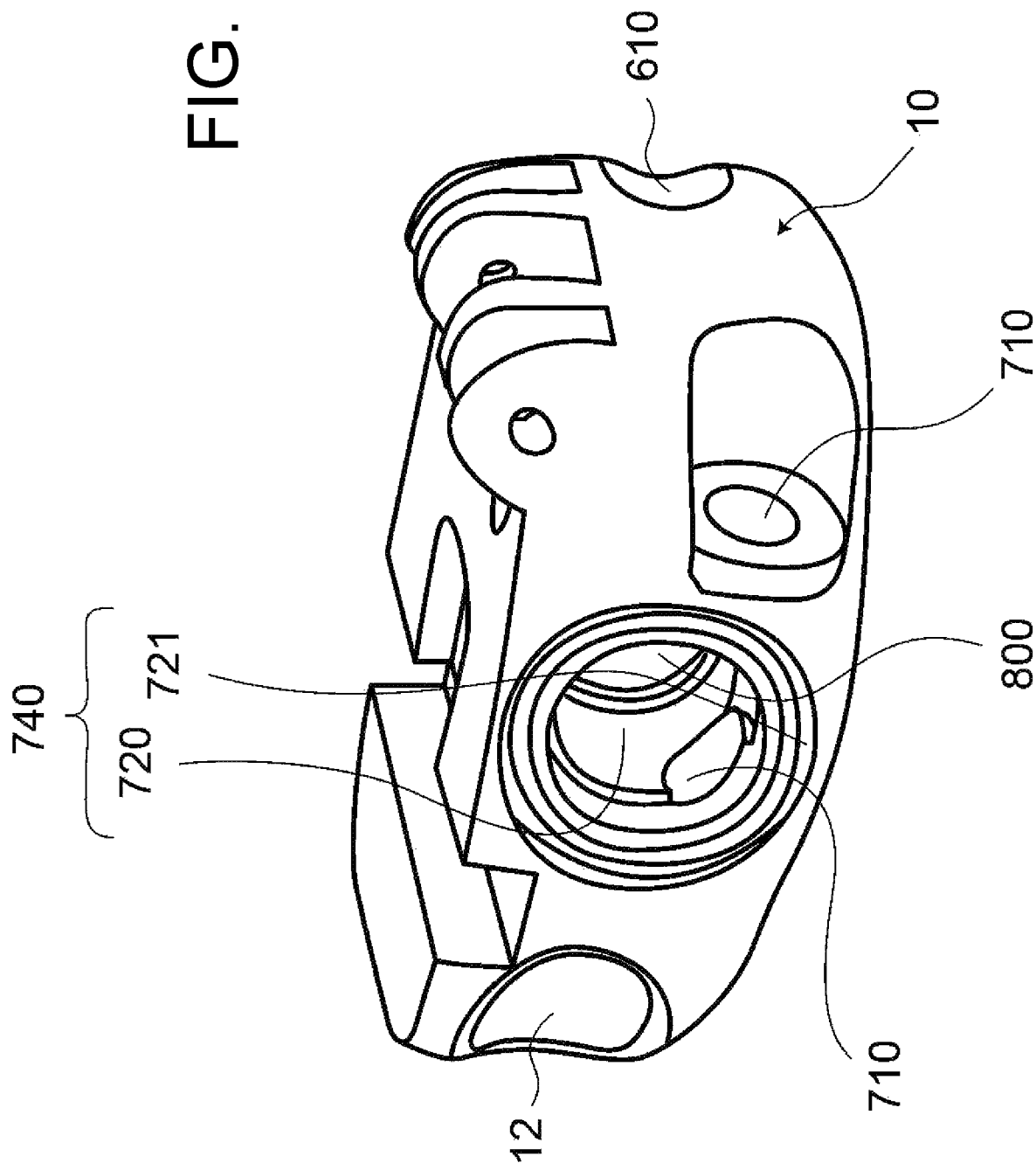
FIG. 13 is a schematic perspective view illustrating a suction device body as viewed from the side opposite to the flexible tube-provided side.

FIG. 13 is a schematic perspective view illustrating the suction device body 10 as viewed from the side opposite to the flexible tube-provided side.

A conversion mechanism used in the present invention includes the second opening/closing joining member 70, a rotation drum 71, a second rotation joining member 73 and an irrigation path internal joining member 74.

Also, the second switch mechanism used in the present invention includes a closing valve 80.

The closing valve 80 includes at least a closing portion 81, open side surfaces 82 and an irrigation path internal joining member contact portion 83.

The closing valve 80 can move in a longitudinal direction (horizontal direction in FIGS. 11 and 12) of an irrigation path 710 inside the irrigation path 710 via a conversion mechanism that converts opening/closing motion of the rotation lever 20 into linear motion in the longitudinal direction of the irrigation path 710.

Movement of the closing portion 81 of the closing valve 80 in the longitudinal direction of the irrigation path 710 inside the irrigation path 710 enables switching between communication and closing of the irrigation path 710.

As illustrated in FIG. 11, when the rotation lever 20 is open, that is, when no external force is applied to the rotation lever 20, the open side surfaces 82 of the closing valve 80 are housed on the downstream side and the closing portion 81 of the closing valve 80 and an annular elastic body 84 such as an O-ring close the irrigation path 710.

The closing valve 80 is pressed by elastic repulsive means 90, a spring being illustrated as an example thereof, from the irrigation connection portion 40a, 40b side (see FIGS. 1 to 3). The elastic repulsive means 90 allows the open side surfaces 82 of the closing valve 80 to be housed on the downstream side, enabling maintaining a state in which the closing valve 80 closes the irrigation path 710.

Upon the rotation lever 20 being pressed by, e.g., a finger of a surgeon, the second opening/closing joining member 70 illustrated in FIG. 12 is pressed down. The second rotation joining member 73 is movably joined to the second opening/closing joining member 70.

Upon the second opening/closing joining member 70 being pressed down, the second rotation joining member 73 moves. The movement is transmitted from the second rotation joining member 73 to the rotation drum 71, whereby the rotation drum 71 rotates.

The irrigation path internal joining member 74 is movably joined to the rotation drum 71. Upon rotation of the rotation drum 71, the irrigation path internal joining member 74 makes linear motion along the longitudinal direction of the irrigation path 710.

The irrigation path internal joining member 74 includes a closing valve push-out portion 74a and a closing valve pull-back portion 74b.

As a result of rotation of the rotation drum 71, the irrigation path internal joining member 74 moves toward the upstream side of the irrigation path 710, that is, the side of the irrigation path 710 from which liquid flows into the suction device body 10.

However, even if the irrigation path internal joining member 74 moves toward the upstream side of the irrigation path 710, the closing portion 81 of the closing valve 80 does not immediately move to the upstream side of the irrigation path 710.

There is a gap between the closing valve push-out portion 74a of the irrigation path internal joining member 74 and the irrigation path internal joining member contact portion 83 of the closing valve 80. As long as the gap exists, the closing valve push-out portion 74a of the irrigation path internal joining member 74 and the irrigation path internal joining member contact portion 83 of the closing valve 80 are not in contact with each other, and thus, the closing valve 80 is kept closed.

Upon the closing valve push-out portion 74a of the irrigation path internal joining member 74 and the irrigation path internal joining member contact portion 83 of the closing valve 80 coming into contact with each other along with the movement of the irrigation path internal joining member 74 toward the upstream side of the irrigation path 710, the closing valve push-out portion 74a of the irrigation path internal joining member 74 pushes the irrigation path internal joining member contact portion 83 of the closing valve 80 from then on.

Upon the irrigation path internal joining member contact portion 83 being pushed, the closing portion 81 of the closing valve 80, the closing portion 81 closing the irrigation path 710, is moved away from a position at which the closing portion 81 closes the irrigation path 710.

Upon the irrigation path internal joining member contact portion 83 being further pushed, the open side surfaces 82 of the closing valve 80, the open side surfaces 82 having been in close contact with the inside of the irrigation path 710 with no gap, are exposed inside the irrigation path 710.

Upon the open side surfaces 82 of the closing valve 80 being exposed inside the irrigation path 710, the open side surfaces 82 communicate with both of the upstream side and the downstream side with reference to the closing portion 81 of the irrigation path 710.

As a result, liquid can flow from the upstream side of the irrigation path 710 toward the downstream side of the irrigation path 710 through the open side surfaces 82 of the closing valve 80.

With the above-described operation, the surgeon can start irrigation via the flexible tube 30.

Upon the irrigation path internal joining member contact portion 83 being further pushed, a ratio of an exposed part of the open side surfaces 82 of the closing valve 80 in the irrigation path 710 increases, enabling increase in volume of the liquid flowing in the irrigation path 710.

On the other hand, upon the force pressing the rotation lever 20 being lessened, the rotation lever 20 and the suction device body 10 are opened from each other by means of an action of the elastic repulsive means 15 (see FIG. 5) such as torsion springs, whereby the rotation drum 71 rotates reversely.

Upon the reverse rotation of the rotation drum 71, the closing portion 81 of the closing valve 80 is pressed by the elastic repulsive means 90 such as a spring and thereby moves to the downstream side of the irrigation path 710.

The annular elastic body 84 such as an O-ring formed of, e.g., rubber or silicone is provided on the closing portion 81 of the closing valve 80.

Upon the closing portion 81 of the closing valve 80 closing the inside of the irrigation path 710, the closing valve pull-back portion 74b of the irrigation path internal joining member 74 causes the irrigation path internal joining member contact portion 83 of the closing valve 80 to be pulled and thereby deforms the annular elastic body 84. Here, the open side surfaces 82 of the closing valve 80 are housed on the downstream side of the irrigation path 710, and the gap between the closing portion 81 of the closing valve 80 and the irrigation path 710 is thereby eliminated.

When the gap between the closing portion 81 of the closing valve 80 and the irrigation path 710 has been eliminated, the liquid flowing into the suction device body 10 is completely blocked on the upstream side.

Consequently, supply of the liquid to the flexible tube 30 can be stopped. Also, liquid pressure is prevented from being applied to both the first switch mechanism and the conversion mechanism located downstream of the closing portion 81 of the closing valve 80.

A conventional irrigation function-equipped suction device has a structure that shuts off a liquid flow via a rotation valve, a piston valve or the like. In the case of this structure, liquid pressure is directly applied to movable parts, and thus, it is extremely difficult to achieve both a smooth operation of the rotation valve, the piston valve or the like and prevention of liquid leakage from a gap at an interface with the rotation valve or the piston valve.

On the other hand, in the case of the irrigation function-equipped suction device 100 according to Embodiment 1, no liquid pressure is applied to both the first switch mechanism and the conversion mechanism located downstream of the closing portion 81 of the closing valve 80, enabling prevention of liquid leakage from a gap at an interface with the first switch mechanism and a gap at an interface with the conversion mechanism.

As described above, even if the irrigation path internal joining member 74 moves toward the upstream side of the irrigation path 710, the closing portion 81 does not immediately start moving. Until the closing valve push-out portion 74a of the irrigation path internal joining member 74 and the irrigation path internal joining member contact portion 83 of the closing valve 80 come into contact with each other, the closing portion 81 keeps closing the irrigation path 710.

Adjustment of the gap between the closing valve push-out portion 74a of the irrigation path internal joining member 74 and the irrigation path internal joining member contact portion 83 of the closing valve 80 enables control of an operation of starting communication of the irrigation path 710 upon the suction path 610 being closed, and closing the irrigation path 710 upon the suction path 610 being brought into communication.

As a material of the suction device body 10, for example, a metal material such as stainless steel, titanium, aluminum or any of alloys thereof, an organic material such as engineering plastic or a thermosetting resin, or an inorganic material such as ceramic can be used.

From the perspective of operability and durability, the material of the suction device body 10 is preferably a metal, more preferably stainless steel. The same applies to materials of parts other than the suction device body 10 except flexible parts.

Also, a material of the flexible tube 30 is preferably flexible stainless steel.

As illustrated in FIGS. 11 to 13, in the suction device body 10, the irrigation path 710 is provided in parallel with the suction path 610. The hollow cavity 720 for inserting the rotation drum 71 is provided at an intermediate position in the irrigation path 710.

The irrigation path 710 is flexed in an L-shape on the downstream side relative to the hollow cavity 720 (see reference sign 710a in FIGS. 11 and 12) and communicates with the suction path 610 via a connection portion 711.

A second opening/closing joining member insertion hole 730 for inserting the second opening/closing joining member 70 from the upper side in FIGS. 11 and 12 is provided in the suction device body 10.

Also, a second opening/closing joining member insertion groove 731 for movably housing the second rotation joining member 73 is provided in the suction device body 10.

The hollow cavity 720, the second opening/closing joining member insertion hole 730 and the second opening/closing joining member insertion groove 731 form a second section 740.

Figure 14:
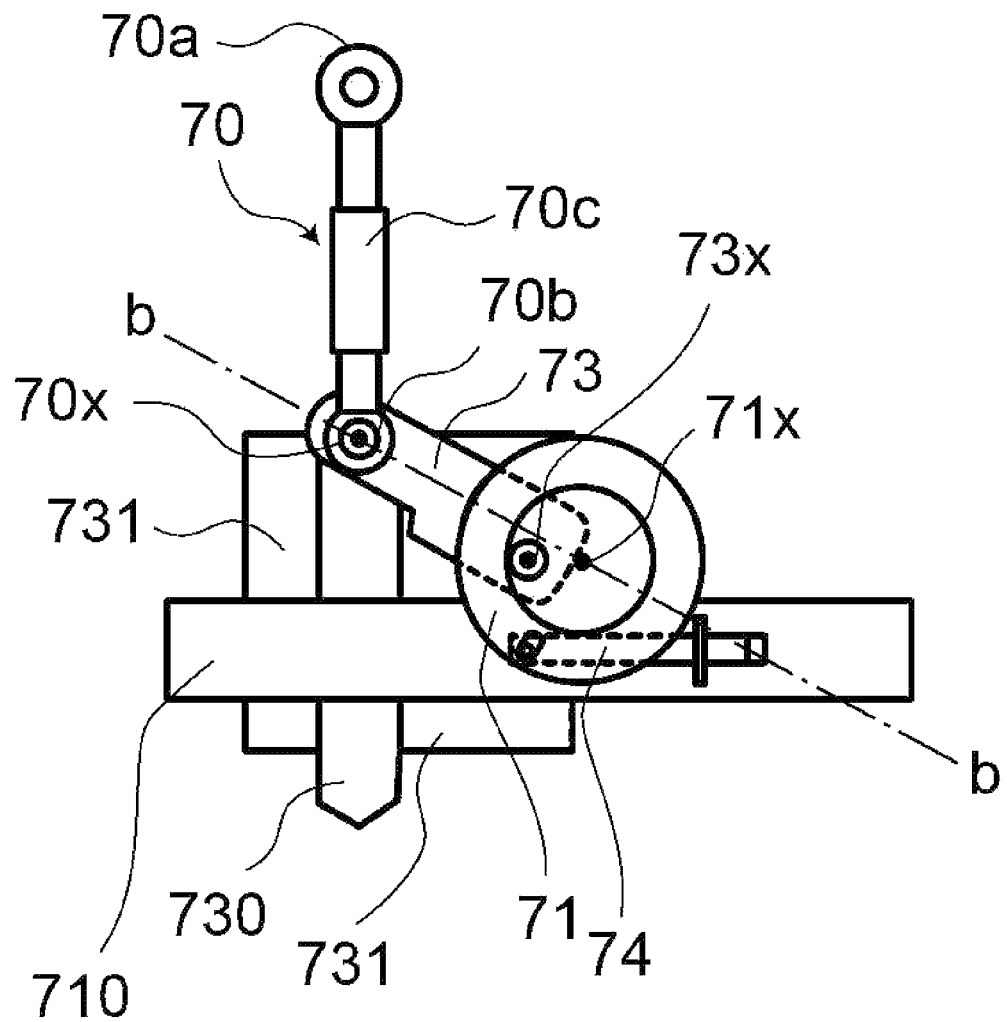
FIG. 14 is a schematic partial view for describing an interlocking relationship among a second opening/closing joining member, a second rotation joining member and a rotation drum.

The second opening/closing joining member 70 is inserted in the second section 740 so as to be movable in the vertical direction in FIG. 14. The second opening/closing joining member 70 is movably joined to the second rotation joining member 73. Also, the second rotation joining member 73 is movably joined to the rotation drum 71.

An annular elastic body 75 such as an O-ring is provided on the rotation drum 71. A cover body 76 (see FIGS. 1 to 3) including a screw portion is screwed from the outside into a screw groove 721 provided inside the hollow cavity 720.

Based on a plane perpendicular to the vertical direction in FIGS. 11 and 12, that is, a plane perpendicular to a longitudinal direction of the second opening/closing joining member insertion hole 730, a part of the irrigation path 710, the part being in parallel with the suction path 610, is preferably provided on the lower side relative to the suction path 610, that is, the bottom side of the suction device body 10.

As a result of the part of the irrigation path 710, the part being in parallel with the suction path 610, being provided on the lower side relative to the suction path 610, upper limit motion of the second opening/closing joining member 70 can more largely be converted to forward/backward motion of the closing valve 80 along the longitudinal direction of the irrigation path 710.

Each of the first section 640 and the second section 740 can be formed by hollowing out the material such as a metal by means of, e.g., a cutting process, and there is a partition wall portion 800 between the hollow cavities 620, 720 of the suction device body 10.

Thus, even if leakage of liquid occurs in the second section 740 that is in contact with the irrigation path 710, the partition wall portion 800 can prevent the leaked liquid from being endlessly sucked to the upstream side of the suction path 610.

Figure 15:
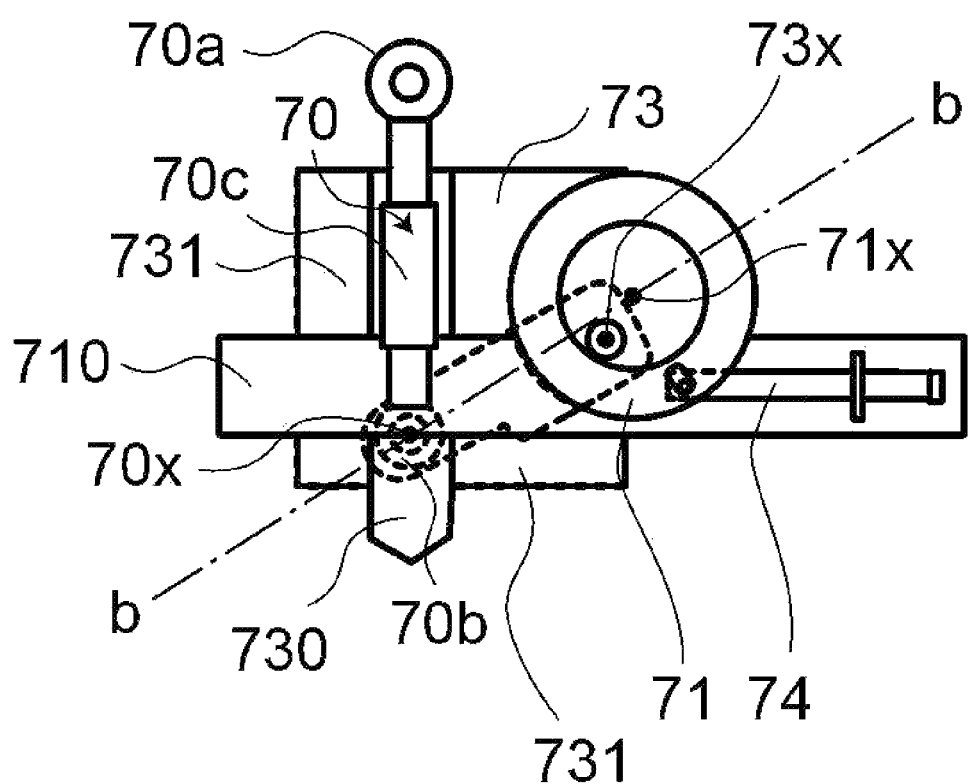
FIG. 15 is a schematic partial view for describing an interlocking relationship among the second opening/closing joining member, the second rotation joining member and the rotation drum.

FIGS. 14 and 15 are schematic partial views for describing an interlocking relationship among the second opening/closing joining member, the second rotation joining member and the rotation drum.

As illustrated in FIGS. 14 and 15, the second rotation joining member 73 and the rotation drum 71 are movably joined to each other at a position on the side opposite to the second opening/closing joining member 70 relative to a straight line connecting a joining axle 70x between the second opening/closing joining member 70 and the second rotation joining member 73 and a center axis 71x of the rotation drum 71 (alternate long and short dash line b-b).

As described above, as a result of the second rotation joining member 73 and the rotation drum 71 being movably joined at a position on the side opposite to the second opening/closing joining member 70 relative to the straight line connecting the joining axle 70x between the second opening/closing joining member 70 and the second rotation joining member 73 and the center axis 71x of the rotation drum 71, vertical motion of the second opening/closing joining member 70 is smoothly converted into linear motion of the irrigation path internal joining member 74.

The second opening/closing joining member 70 includes an opening/closing joining member body portion 70c, and curve surface portions 70a, 70b provided at opposite ends of the joining member body portion 70c.

Based on a cross-section perpendicular to a longitudinal direction of the opening/closing joining member body portion 70c, that is, the vertical direction in FIGS. 14 and 15, a largest cross-section of each of the curve surface portions 70a, 70b is larger than a largest cross-section of the opening/closing joining member body portion 70c.

As observed in the longitudinal direction of the opening/closing joining member body portion 70c, the largest cross-section of the opening/closing joining member body portion 70c is located within each of the respective largest cross-sections of the curve surface portions 70a, 70b.

Provision of the curve surface portions 70a, 70b allows the second opening/closing joining member 70 to smoothly move along the inside of the second opening/closing joining member insertion hole 730 provided inside the suction device body 10.

As described above, the first section 640 and the second section 740 communicate with each other only via the connection portion 711 between the irrigation path 710 and the suction path 610 inside the suction device body 10.

Also, the connection portion 711 constantly communicates with atmosphere through the flexible tube 30.

Therefore, even if the irrigation path 710 is closed, excessive liquid pressure can be prevented from being applied to the respective parts provided in the first section 640 and the second section 740.

Accordingly, liquid pressure can be prevented from being applied to both the first switch mechanism and the conversion mechanism located downstream of the closing portion 81 of the closing valve 80.

The present invention enables achievement of both prevention of liquid leakage and smooth switching between a suction operation and an irrigation operation of the irrigation function-equipped suction device 100.

Embodiment 2 of Invention

Next, Embodiment 2 of the present invention, which is an alteration of Embodiment 1 of the present invention, will be described.

An irrigation function-equipped suction device 110 according to Embodiment 2 is an improvement made so that an amount of liquid supplied from a flexible tube 30 (see FIGS. 1 to 3) increases along with an operation of a rotation lever 20.

Figure 16:
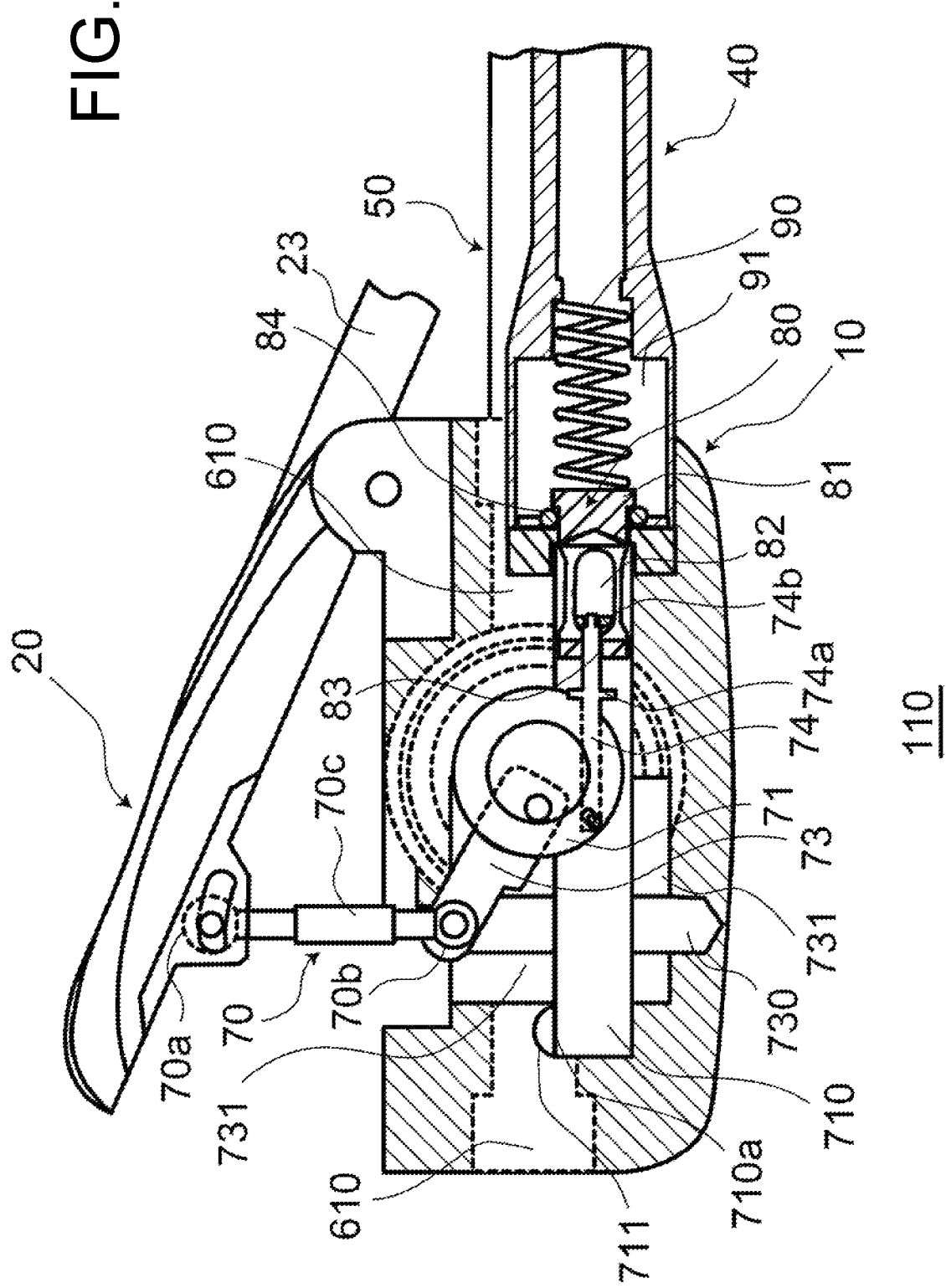
FIG. 16 is a schematic sectional view for describing a second switch mechanism when an irrigation path and a flexible tube are closed off from each other in Embodiment 2.
Figure 17:
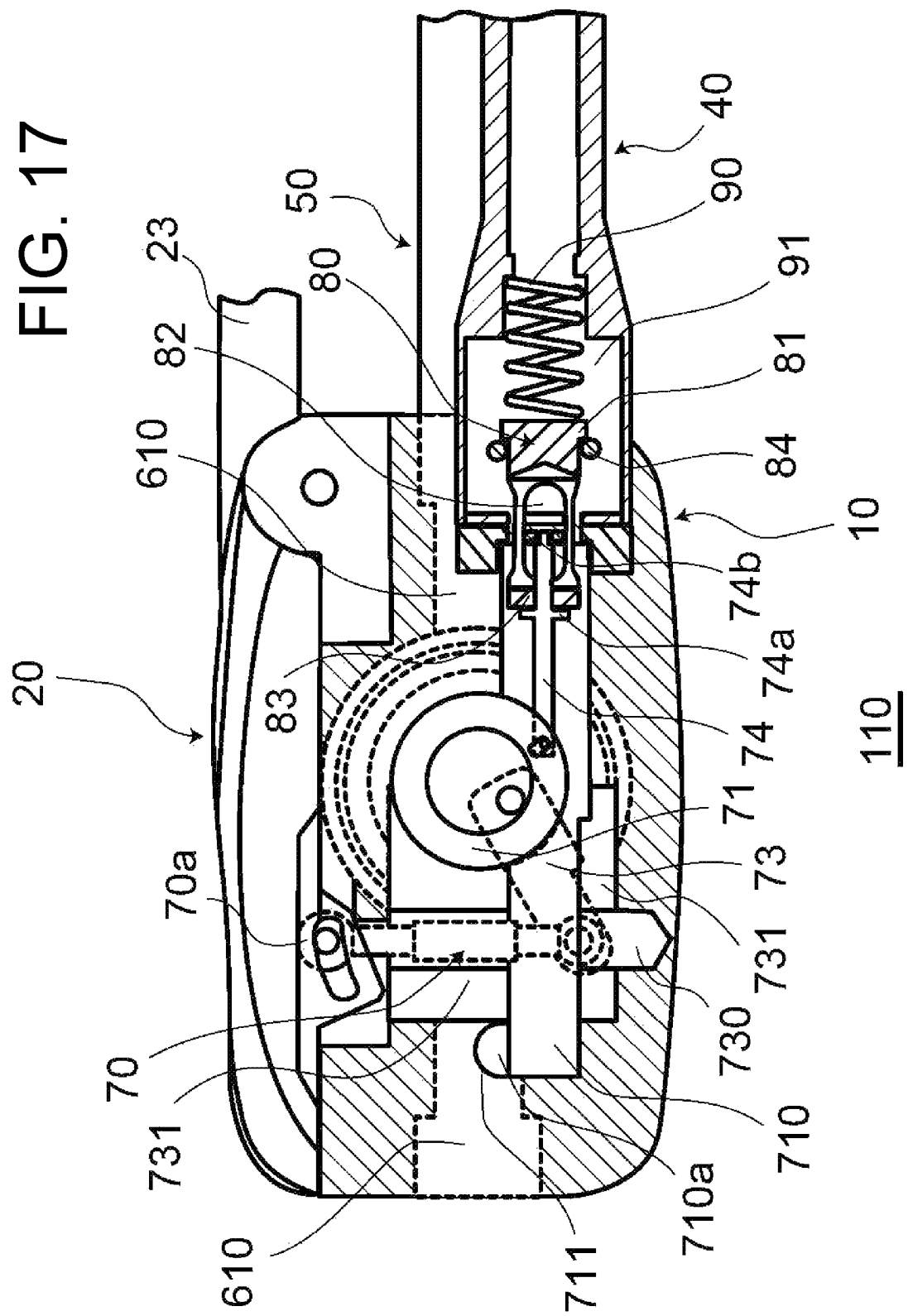
FIG. 17 is a schematic sectional view for describing the second switch mechanism when the irrigation path and the flexible tube communicate with each other in Embodiment 2.

FIGS. 16 and 17 are schematic sectional views for describing an operation status of a second switch mechanism that makes switching to cause an irrigation path and a flexible tube to be closed off from each other or communicate with each other in the irrigation function-equipped suction device 110 according to Embodiment 2.

As in the irrigation function-equipped suction device 100 according to Embodiment 1, a closing valve 80 illustrated in FIGS. 16 and 17 is pressed by elastic repulsive means 90, a spring being illustrated as an example thereof, from the irrigation connection portion 40a, 40b side (see FIGS. 1 to 3). The elastic repulsive means 90 allows open side surfaces 82 of the closing valve 80 to be housed on the downstream side, enabling maintaining a state in which the closing valve 80 closes the irrigation path 710.

Upon the rotation lever 20 being pressed by, e.g., a finger of a surgeon, through an operation as in the case of the irrigation function-equipped suction device 100 according to Embodiment 1 described above, the open side surfaces 82 of the closing valve 80, the open side surfaces 82 having been in close contact with the inside of the irrigation path 710 with no gap, are exposed inside the irrigation path 710.

As a result, liquid can flow from the upstream side of the irrigation path 710 toward the downstream side of the irrigation path 710 through the open side surfaces 82 of the closing valve 80. As in Embodiment 1 described above, supply of liquid to the flexible tube 30 can be started.

In the case of the irrigation function-equipped suction device 110 according to Embodiment 2, the open side surfaces 82 of the closing valve 80 are large relative to the open side surfaces of the closing valve used in Embodiment 1 described above.

Also, based on a section perpendicular to a longitudinal direction of the irrigation path 710, a size of a liquid intake chamber portion 91 inside the irrigation path 710 of the irrigation function-equipped suction device 110 is larger than that of the irrigation path 710.

Based on a plane perpendicular to a straight line along the longitudinal direction of the irrigation path 710, the liquid intake chamber portion 91 is provided at a position on the side opposite to the flexible tube 30 relative to each of the rotation valve 61 included in the first switch mechanism 600 and the rotation drum 71 included in the conversion mechanism.

In addition, the liquid intake chamber portion 91 is large in comparison with a liquid intake chamber portion inside the irrigation path of the irrigation function-equipped suction device 100.

In the case of the irrigation function-equipped suction device 110 according to Embodiment 2, a large amount of liquid can smoothly flow through the open side surfaces 82 of the closing valve 80.

On the other hand, upon the surgeon lessening the force pressing the rotation lever 20, as in Embodiment 1 described above, the supply of liquid to the flexible tube 30 can be stopped.

Embodiment 3 of Invention

Next, Embodiment 3 according to the present invention, which is an alteration of Embodiment 1 of the present invention, will be described.

Figure 18:
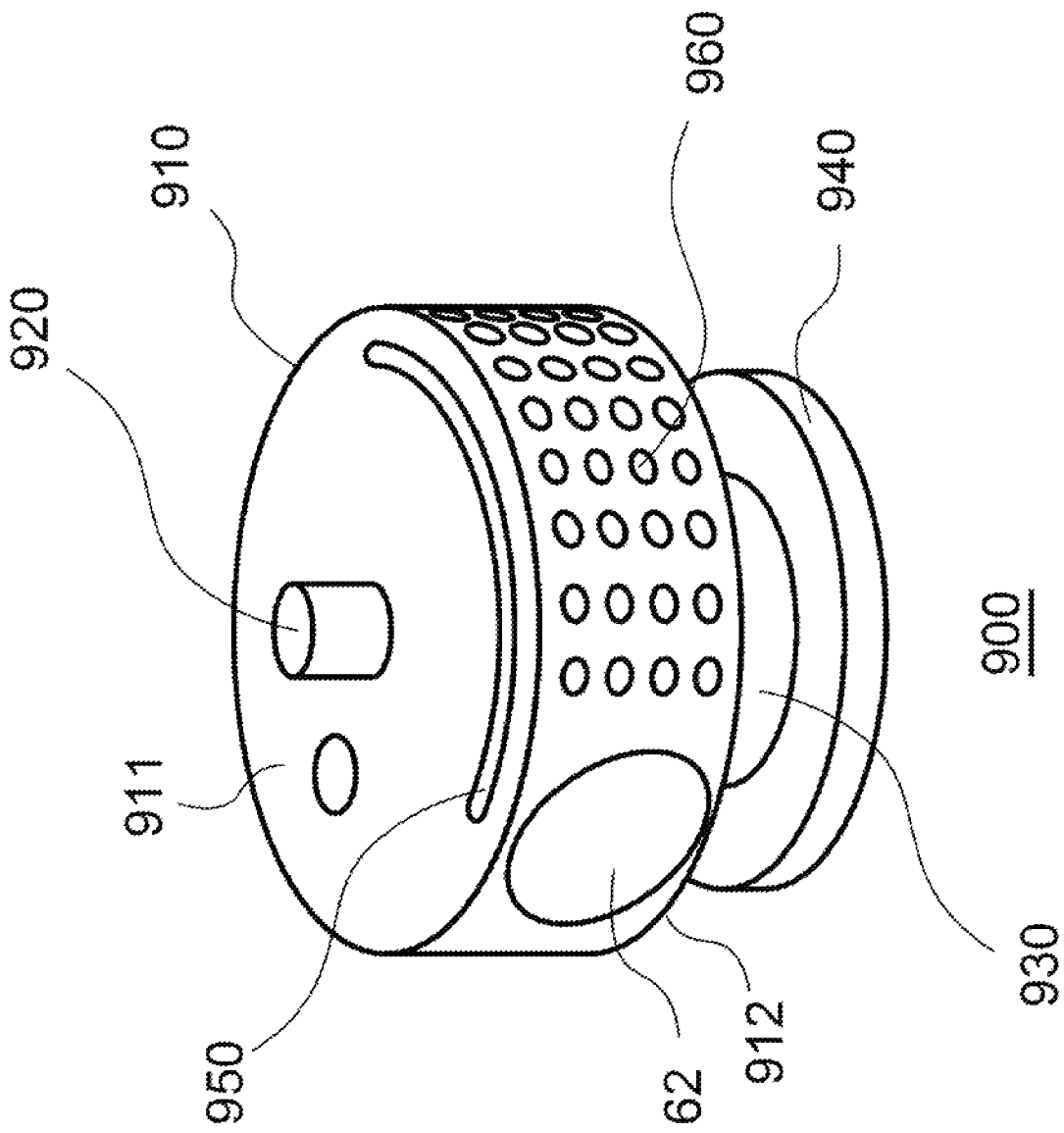
FIG. 18 is a schematic perspective view of a rotation valve used in an irrigation function-equipped suction device according to Embodiment 3.

FIG. 18 is a schematic perspective view of a rotation valve 900 used in an irrigation function-equipped suction device 120 according to Embodiment 3.

The rotation valve 900 includes a rotation valve body 910, rotation shafts 920, 930 and a rotation valve disk 940.

In the rotation valve body 910, a circular cylindrical hollow portion 62 extending through the rotation valve body 910 is provided in a direction perpendicular to a center axis of the rotation shafts 920, 930. Gas, liquid, etc., can be sucked through the hollow portion 62.

Also, a void 950 is provided in the rotation valve body 910. The void 950 is located inside the rotation valve body 910 and extends through an outer surface 911 and an inner surface 912 of the rotation valve body 910.

The void 950 only needs to be provided inside the rotation valve body 910 and a shape of the void 950 is not limited.

The void 950 is provided inside the rotation valve body 910 so as to avoid the hollow portion 62. Therefore, none of liquid, gas, etc., can travel between the void 950 and the hollow portion 62.

On the other hand, in the rotation valve body 910, vent holes 960 that lead from the outside of the rotation valve body 910 to the void 950 are provided in a direction perpendicular to the center axis of the rotation shafts 920, 930.

Although in the rotation valve 900 illustrated in FIG. 18, a plurality of circular cylindrical vent holes 960 are illustrated, it is only necessary that at least one vent hole 960 of the vent holes 960 leads to the void 950 and it is more preferable that all of the vent holes 960 lead to the void 950.

Also, the shape of the vent holes 960 is not limited to a circular cylindrical shape, and may be, for example, a polygonal cylindrical shape or an elliptic cylindrical shape.

Figure 19:
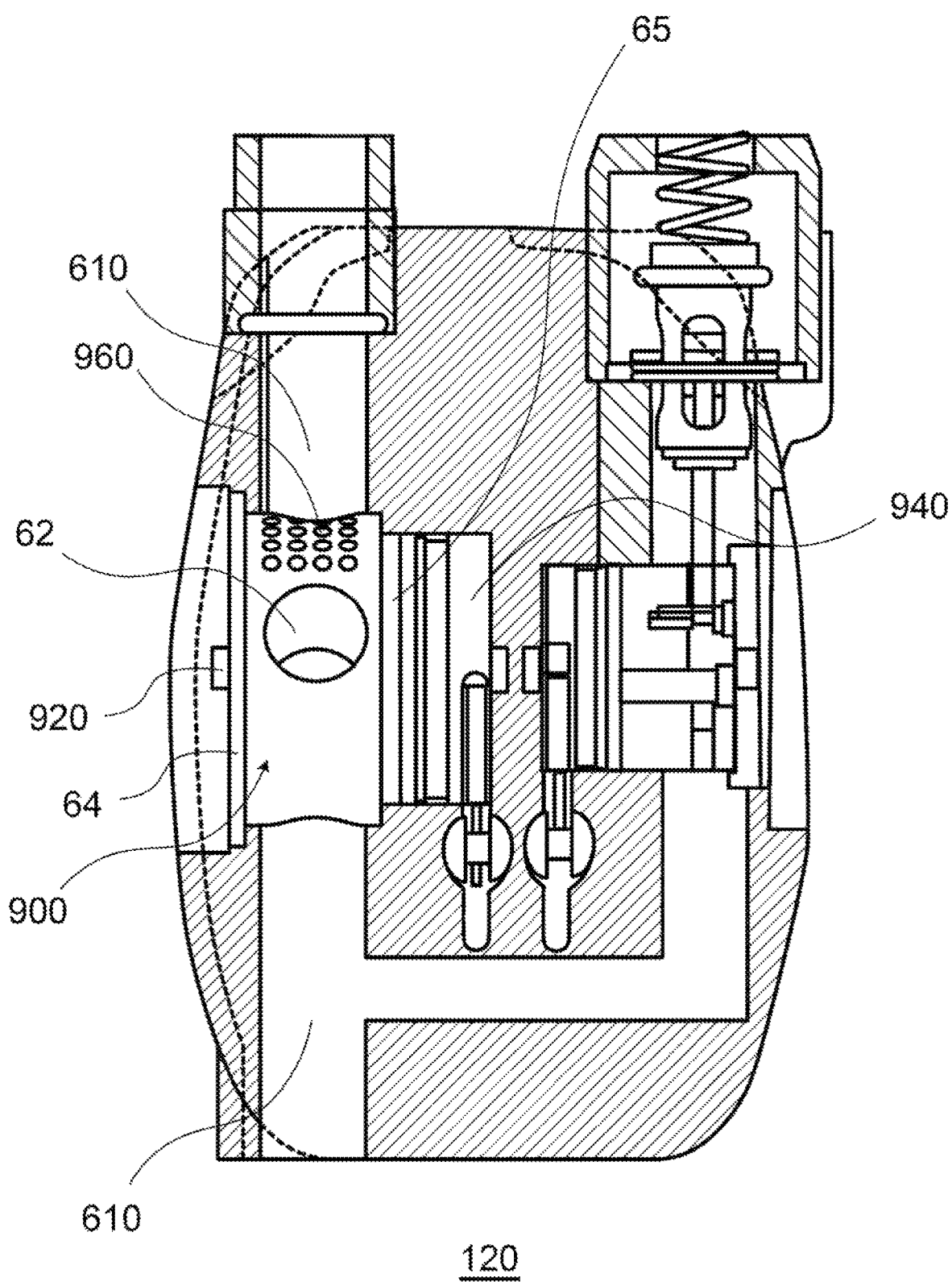
FIG. 19 is a schematic partial sectional view for describing a function of the rotation valve.
Figure 20:
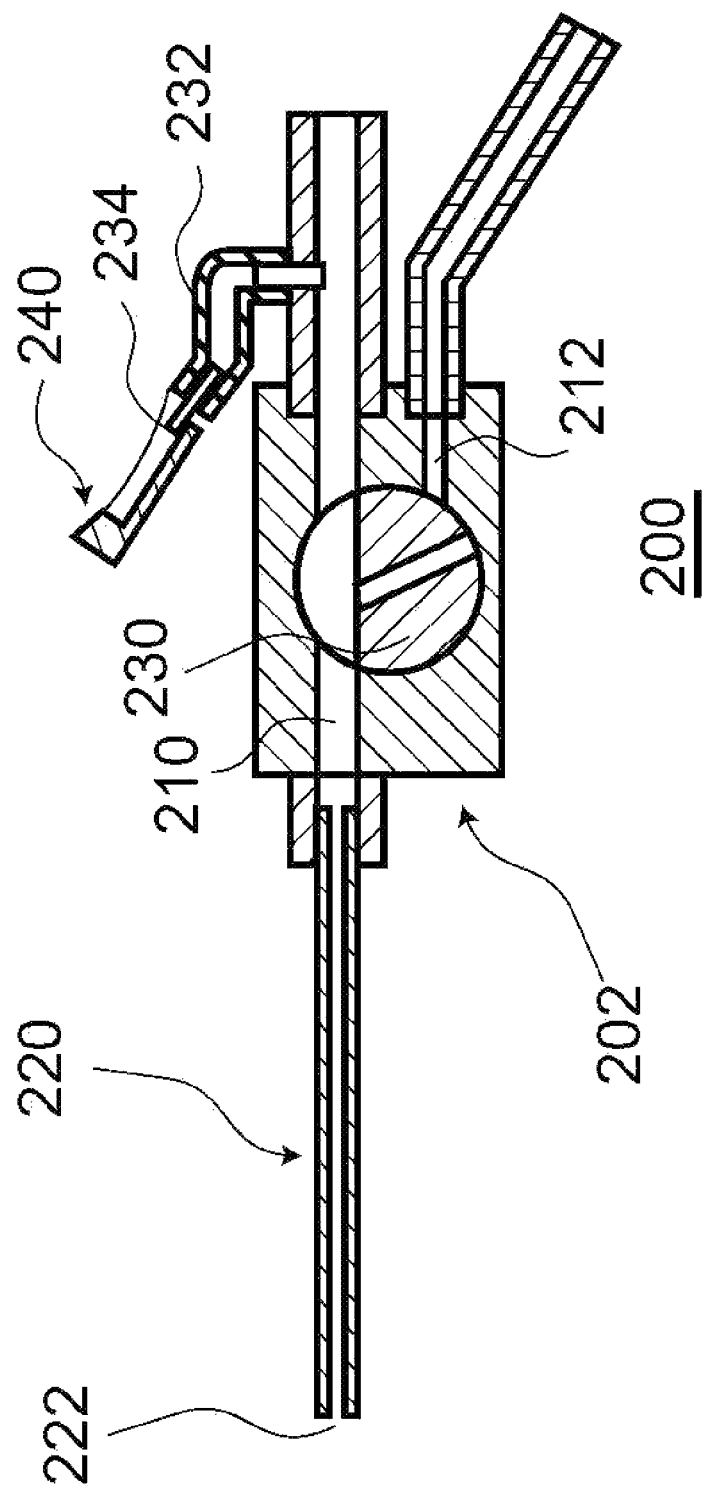
FIG. 20 is a schematic sectional view of an irrigation function-equipped suction device according to a third conventional technique.
Figure 21:
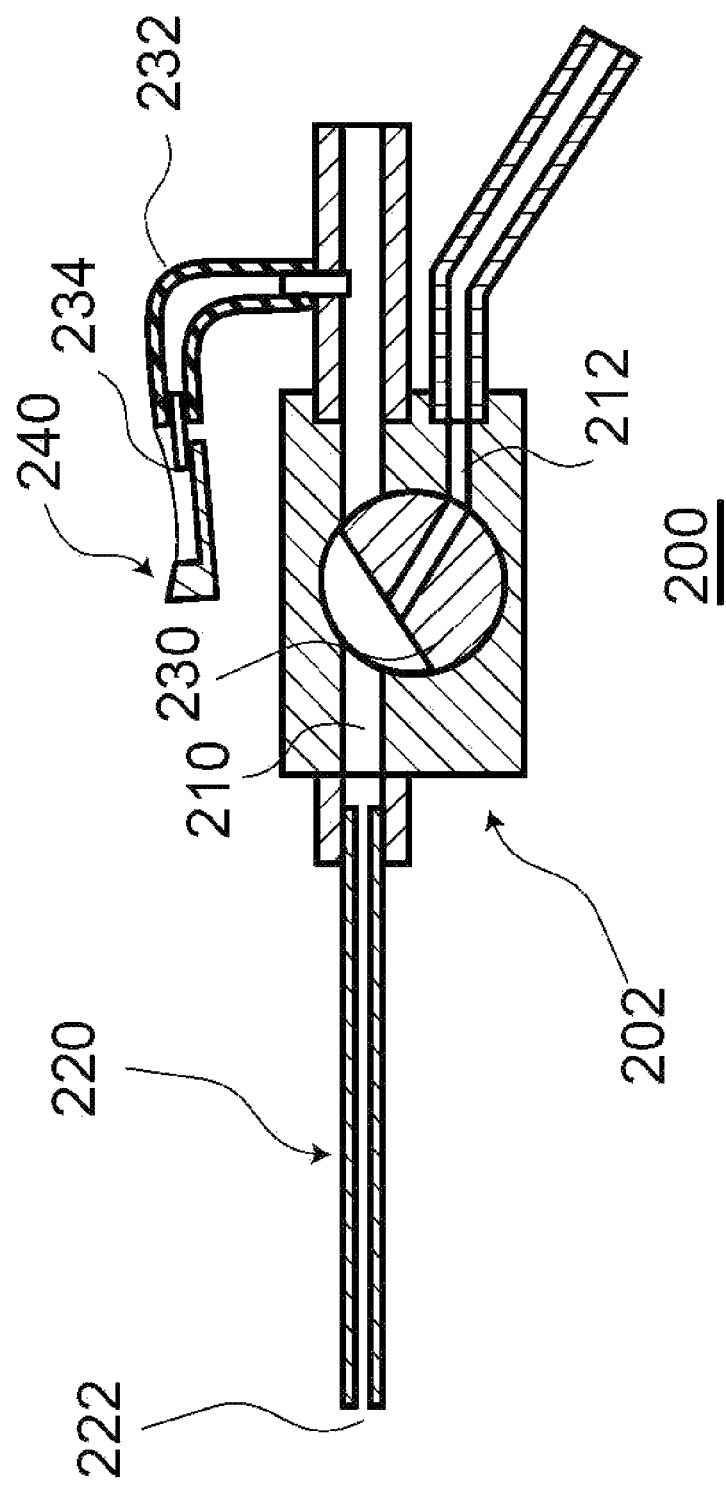
FIG. 21 is a schematic sectional view of the irrigation function-equipped suction device according to the third conventional technique.

FIG. 19 is a schematic partial sectional view for describing a function of the rotation valve 900. As in the case of FIGS. 3 and 7 used for description of Embodiment 1 above, FIG. 19 illustrates a state when the rotation lever 20 is closed.

When the rotation lever 20 is closed, the hollow portion 62 of the rotation valve 900 is closed and the hollow portion 62 and the suction path 610 are not connected.

On the other hand, the vent holes 960 are exposed inside the suction path 610. The inside of the suction path 610 is connected to the void 950 through the vent holes 960.

Upon the hollow portion 62 and the suction path 610 being connected as a result of the rotation valve 900 being rotated, all of the vent holes 960 are closed.

Based on the area of a part of the rotation valve 900, the part being exposed inside the suction path 610, in comparison with a case where neither the vent holes 960 nor the void 950 exist, where the vent holes 960 and the void 950 exist, when the suction path 610 is depressurized, the surface area subjected to the depressurization is large.

In other words, if the vent holes 960 and the void 950 exist, surface areas of respective insides of the vent holes 960 and the void 950 are added in comparison with the case where neither the vent holes 960 nor the void 950 exist, and thus, even if the suction path 610 is depressurized, a force applied to each unit area of the rotation valve body 910 is small.

Where the vent holes 960 and the void 950 exist in the rotation valve 900, even if the suction path 610 is strongly depressurized, a force applied to the rotation valve 900 can be dispersed, enabling the rotation valve 900 to be smoothly rotated and thus enables opening/closing motion of the rotation lever to be kept smooth.

INDUSTRIAL APPLICABILITY

A irrigation function-equipped suction device according to the present invention can widely be used as a medical instrument for use in the medical field such as brain surgery.

Also, an irrigation function-equipped suction device according to the present invention can widely be used for restoration work for an archaeological material such as antiquities, stratum analysis work, etc., as well as cleaning work and painting work that need cleaning and suction operation.

REFERENCE SIGNS LIST 10, 202 suction device body
11 opening/closing connection portion
12, 22 depression portion
13 joining portion
14 joining long pivot shaft pin
15, 90 elastic repulsive means
20, 240 rotation lever
21 adjustment hole
23 conduction tube
24 elongated hole
25 protrusion portion
26 screw
27 groove portion
30 flexible tube
31 proximal end
32 distal end
33 connection tube
40 irrigation tube
40a, 40b irrigation connection portion
50 suction tube
50a, 50b suction connection portion
51 branch tube
52 connection flexible tube
60 first opening/closing joining member
60a, 60b, 70a, 70b curve surface portion
60c, 70c opening/closing joining member body portion
60x, 63x, 70x, 73x joining axle
61, 900 rotation valve
61x, 71x center axis
62 hollow portion
63 first rotation joining member
64, 65 annular elastic body
66, 76 cover body
70 second opening/closing joining member
71 rotation drum
73 second rotation joining member
74 irrigation path internal joining member
74a closing valve push-out portion
74b closing valve pull-back portion
80 closing valve
81 closing portion
82 open side surface
83 irrigation path internal joining member contact portion
84 annular elastic body
90 elastic repulsive means
91 liquid intake chamber portion
100, 110, 120, 200 irrigation function-equipped suction device
210 suction path
212 irrigation path
220 flexible tube
222 distal end
230 rotation valve
232 flexible tube
234 suction pressure fine adjustment hole
600 first switch mechanism
610 suction path
620, 720 hollow cavity
621 screw groove
630 first opening/closing joining member insertion hole
631 first rotation joining member installation groove
640 first section
710 irrigation path
710a L-shaped flexed portion of irrigation path
711 connection portion
730 second opening/closing joining member insertion hole
731 second rotation joining member installation groove
740 second section
800 partition wall portion
910 rotation valve body
911 outer surface
912 inner surface
920, 930 rotation shaft
940 rotation valve disk
950 void
960 vent hole

The invention claimed is:
1. An irrigation function-equipped suction device including:
a suction device body;
a rotation lever provided so as to be capable of being opened or closed relative to the suction device body;
a suction path provided in the suction device body;
an irrigation path provided in the suction device body;

a flexible tube having a proximal end attached to a distal end of the suction device body, a distal end of the flexible tube being directed to a surgical site;

a first switch mechanism including a rotation valve, the first switch mechanism making switching to cause the suction path and the flexible tube to communicate with each other or be closed off from each other;

a second switch mechanism including a closing valve, the second switch mechanism making switching to cause the irrigation path and the flexible tube to communicate with each other or be closed off from each other; and a conversion mechanism that causes opening/closing motion of the rotation lever to be converted into linear motion along a longitudinal direction of the irrigation path by rotational motion of a rotation drum to move the closing valve, wherein:

if the suction path and the flexible tube are brought into communication with each other by the first switch mechanism, the irrigation path is closed by the second switch mechanism and the conversion mechanism;

if the suction path is closed by the first switch mechanism, the irrigation path and the flexible tube are brought into communication with each other by the second switch mechanism and the conversion mechanism;

the first switch mechanism is provided in a first section inside the suction device body;

the second switch mechanism and the conversion mechanism are provided in a second section inside the suction device body;

an irrigation path internal joining member included in the conversion mechanism, the irrigation path internal joining member making linear motion along the longitudinal direction of the irrigation path, is provided inside the irrigation path;

the irrigation path is connected to the suction path at a position on the flexible tube side relative to the rotation valve included in the first switch mechanism and the rotation drum included in the conversion mechanism, based on a plane perpendicular to a linear line along the longitudinal direction of the irrigation path; and the closing valve included in the second switch mechanism is disposed at a position on a side opposite to the flexible tube relative to the rotation valve included in the first switch mechanism and the rotation drum included in the conversion mechanism, based on the plane perpendicular to the linear line along the longitudinal direction of the irrigation path.

2. The irrigation function-equipped suction device according to claim 1, wherein if the irrigation path is closed by the second switch mechanism, a path for communication with atmosphere is kept for the conversion mechanism.

3. The irrigation function-equipped suction device according to claim 2, wherein:

the second switch mechanism includes:

the closing valve that closes the irrigation path, and the irrigation path internal joining member that makes linear motion along the longitudinal direction of the irrigation path relative to the closing valve, along with an operation of the conversion mechanism; and wherein the rotation drum controls movement and stoppage of the closing valve during the linear motion of the irrigation path internal joining member.

4. The irrigation function-equipped suction device according to claim 3, including:

a first opening/closing joining member and a second opening/closing joining member each movably joined to the rotation lever;

a first rotation joining member movably joined to the first opening/closing joining member, the rotation valve being movably joined to the first rotation joining member; and a second rotation joining member movably joined to the second opening/closing joining member, the rotation drum being movably joined to the second rotation joining member;

wherein:

the irrigation path internal joining member is movably joined to the rotation drum, along with an operation of insertion of the first opening/closing joining member to the first section, the rotation valve rotates and thereby closes the suction path, along with an operation of insertion of the second opening/closing joining member to the second section, the rotation drum rotates and thereby brings the irrigation path into communication, subsequent to the closing of the suction path, the irrigation path is brought into communication, along with an operation of the first opening/closing joining member being pulled out from the first section, the rotation valve rotates and thereby brings the suction path into communication, along with an operation of the second opening/closing joining member being pulled out from the second section, the rotation drum rotates and thereby closes the irrigation path, and subsequent to the closing of the irrigation path, the suction path is brought into communication are provided.

5. The irrigation function-equipped suction device according to claim 4, wherein:

the irrigation path internal joining member includes a closing valve push-out portion and a closing valve pull-back portion;

the closing valve includes a closing portion, an open side surface and an irrigation path internal joining member contact portion;

the closing valve push-out portion and the closing valve pull-back portion are provided in the irrigation path internal joining member in such a manner that the closing valve push-out portion and the closing valve pull-back portion are spaced from each other;

if the irrigation path internal joining member moves to a side of the suction device body opposite to a flexible tube-provided side of the suction device body, the closing valve push-out portion of the irrigation path internal joining member comes into contact with the irrigation path internal joining member contact portion of the closing valve, the closing valve is pushed out to the side of the suction device body opposite to the flexible tube-provided side of the suction device body, closing of the irrigation path by the closing valve is cancelled, and the open side surface of the closing valve is exposed inside a part of the irrigation path on the side of the suction device body opposite to the flexible tube-provided side of the suction device body and the irrigation path is thereby brought into communication, and if the irrigation path internal joining member moves to the flexible tube-provided side of the suction device body, the closing valve pull-back portion of the irrigation path internal joining member comes into contact with the irrigation path internal joining member contact portion of the closing valve, the closing valve is pulled back to the flexible tube-provided side of the suction device body and the irrigation path is closed by the closing valve.

6. The irrigation function-equipped suction device according to claim 5, wherein:

the closing valve is pressed to the suction device body side from the outer side of the suction device body by a repulsive force of an elastic body, during linear motion of the irrigation path internal joining member, if there is a space between the closing valve push-out portion of the irrigation path internal joining member and the irrigation path internal joining member contact portion of the closing valve, the closing valve keeps closing the irrigation path.

7. The irrigation function-equipped suction device according to claim 6, wherein:

the rotation lever includes a depression portion, an adjustment hole and a conduction path that brings the rotation lever into communication, the adjustment hole is provided in the depression portion in an outer surface of the rotation lever, an end of the conduction path is connected to the adjustment hole, and another end of the conduction path is connected to the suction path via the flexible tube.

8. The irrigation function-equipped suction device according to claim 4, wherein:

each of the first opening/closing joining member and the second opening/closing joining member includes an opening/closing joining member body portion; and a curve surface portion provided at each of opposite ends of both of the opening/closing joining member body portions, and based on a cross-section perpendicular to a longitudinal direction of each of the opening/closing joining member body portions, a largest cross-section of each of the curve surface portions is larger than a largest cross-section of each of the opening/closing joining member body portions, and as observed in the longitudinal direction of each of the opening/closing joining member body portions, the largest cross-section of each of the opening/closing joining member body portions is located within the largest cross-section of each of the curve surface portions.

9. The irrigation function-equipped suction device according to claim 4, wherein:

the rotation valve includes a hollow portion, a void provided inside the rotation valve, and a vent hole that makes the void and an outside of the rotation valve communicate with each other, neither the void nor the vent hole communicates with the hollow portion inside the rotation valve, and when the suction path and the flexible tube are closed off from each other, the vent hole is exposed in the suction path.

* * * * *